(12) United States Patent
Ramsay et al.

(10) Patent No.: US 9,504,494 B2
(45) Date of Patent: Nov. 29, 2016

(54) IMPLANTS FOR SECURING SPINAL FIXATION ELEMENTS

(75) Inventors: Christopher L. Ramsay, West Wareham, MA (US); Sara Dziedzic, Dorchester, MA (US); Michael Mahoney, Middletown, RI (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 1169 days.

(21) Appl. No.: 12/110,823

(22) Filed: Apr. 28, 2008

(65) Prior Publication Data

US 2009/0270916 A1 Oct. 29, 2009

(51) Int. Cl.
*A61B 17/70* (2006.01)
*A61B 17/17* (2006.01)

(52) U.S. Cl.
CPC ....... *A61B 17/7037* (2013.01); *A61B 17/1735* (2013.01); *A61B 2090/037* (2016.02)

(58) Field of Classification Search
CPC ................ A61B 17/7083–17/7089; A61B 17/8605–17/862
USPC ........ 606/246, 264–268, 270, 272–274, 300, 606/305, 279, 86 A, 99
See application file for complete search history.

(56) References Cited

U.S. PATENT DOCUMENTS

| | | | | |
|---|---|---|---|---|
| 5,863,293 A * | 1/1999 | Richelsoph | | 606/278 |
| 6,786,907 B2 * | 9/2004 | Lange | | 606/250 |
| 7,160,300 B2 * | 1/2007 | Jackson | | 606/273 |
| 7,491,208 B2 * | 2/2009 | Pond et al. | | 606/104 |
| 7,727,260 B2 * | 6/2010 | Albert et al. | | 606/259 |
| 7,758,584 B2 * | 7/2010 | Bankoski et al. | | 606/104 |
| 7,794,477 B2 * | 9/2010 | Melkent et al. | | 606/246 |
| 8,057,518 B2 * | 11/2011 | Frasier et al. | | 606/267 |
| 2003/0144664 A1 * | 7/2003 | Cavagna et al. | | 606/61 |
| 2006/0184178 A1 * | 8/2006 | Jackson | A61B 17/7032 | 606/99 |
| 2006/0217719 A1 * | 9/2006 | Albert | A61B 17/7011 | 606/261 |
| 2006/0282074 A1 * | 12/2006 | Renaud et al. | | 606/61 |
| 2007/0100341 A1 * | 5/2007 | Reglos | A61B 17/7004 | 606/86 A |
| 2007/0270818 A1 * | 11/2007 | Rezach | | 606/61 |
| 2007/0288002 A1 * | 12/2007 | Carls et al. | | 606/61 |
| 2008/0172096 A1 * | 7/2008 | Hawkins | | 606/305 |
| 2008/0249570 A1 * | 10/2008 | Carson | A61B 17/7038 | 606/264 |
| 2008/0262545 A1 * | 10/2008 | Simonson | | 606/247 |
| 2009/0062858 A1 * | 3/2009 | Dziedzic et al. | | 606/278 |
| 2009/0062864 A1 * | 3/2009 | Ludwig et al. | | 606/301 |
| 2009/0105756 A1 * | 4/2009 | Richelsoph | | 606/246 |
| 2009/0228051 A1 * | 9/2009 | Kolb et al. | | 606/305 |
| 2010/0094345 A1 * | 4/2010 | Saidha et al. | | 606/250 |
| 2010/0168796 A1 * | 7/2010 | Eliasen et al. | | 606/264 |
| 2010/0211100 A1 * | 8/2010 | Mack | | 606/246 |
| 2010/0249844 A1 * | 9/2010 | Durrani | | 606/259 |
| 2011/0196424 A1 * | 8/2011 | Bishop | | 606/264 |

* cited by examiner

*Primary Examiner* — Eduardo C Robert
*Assistant Examiner* — Michelle C Eckman
(74) *Attorney, Agent, or Firm* — Nelson Mullins Riley & Scarborough LLP

(57) ABSTRACT

Embodiments of the present invention provide an implant having a protrusion. The protrusion aids in the insertion and placement of the implant as well as the spinal fixation element. In certain embodiments the protrusion may be configured as a guide for the insertion of the spinal fixation element as well as closure mechanisms for connecting the spinal fixation element to the implant.

16 Claims, 17 Drawing Sheets

IMPLANTS FOR SECURING SPINAL FIXATION ELEMENTS

FIELD OF INTEREST

The present invention relates to connector devices and methods for use during orthopedic surgery. More particularly, the present invention relates to implants for securing spinal fixation elements (SFE) using minimally invasive surgical techniques.

BACKGROUND

Spinal fixation systems may be used in surgery to align, adjust and/or fix portions of a spinal column, i.e., vertebrae, in a desired spatial relationship relative to each other. Many spinal fixation systems employ a spinal rod for supporting the spine and for properly positioning components of the spine for various treatment purposes. Implants, such as vertebral bone anchors, comprising pins, bolts, screws, and hooks, engage the vertebrae and connect the supporting spinal rod to different vertebrae. Spinal rods can be anchored to specific portions of the vertebra. Since each vertebra varies in shape and size, a variety of anchoring devices have been developed to facilitate engagement of a particular portion of the bone.

Pedicle screw assemblies, for example, have a shape and size that is configured to engage pedicle bone. Such screws typically include a threaded shank that is adapted to be threaded into a vertebra, and a head portion having a spinal fixation element-receiving portion, which, in spinal rod applications, is usually in the form of a U-shaped slot formed in the head portion for receiving the rod. A set-screw, plug, cap or similar type of closure mechanism is used to lock the rod into the rod-receiving portion of the pedicle screw.

In conventional spinal surgery, first, anchoring devices are attached to vertebra, and then a spinal rod is aligned with the anchoring devices and secured. For example, for conventional pedicle screw assemblies, first the engagement portion of each pedicle screw is threaded into a vertebra. Once the pedicle screw assembly is properly positioned, a spinal fixation rod is connected in the rod-receiving portion of each pedicle screw head. The rod is locked into place by tightening a cap or similar type of closure mechanism to securely interconnect each pedicle screw to the fixation rod. This type of conventional spinal surgical technique usually involves making a surgical access opening in the back of the patient that is almost as long as the length of the spinal rod to be implanted. Because exact placement of the screw assemblies depends on a patient's particular bone structure and bone quality, the exact position of all screw assemblies cannot be known until after all the assemblies are positioned. Adjustments, such as bending, are made to the spinal rod to ensure that it aligns with each screw assembly.

Recently, the trend in spinal surgery has been moving toward providing minimally invasive surgical (MIS) devices and methods for implanting spinal fixation elements. In minimally invasive surgical techniques, the anchors and rod are typically inserted through small incisions. For example, the anchors and rod may be delivered percutaneously to an implant site through a small access port such as a cannula. In other methodologies, a mini-open technique may be used to place the spinal fixation system.

However, such minimally invasive procedures introduce other issues. Because the bone anchors and spinal fixation element are inserted through small incisions, such as percutaneous, there is reduced visibility of the surgical site. Placement and mating of the implants and spinal fixation element becomes more difficult when there is no direct view of the surgical site. Thus, what is needed is a means for being able to accurately place and mate a spinal fixation element and implants along a patient's spine when using minimally invasive surgical techniques.

SUMMARY

Embodiments of the present invention provide an implant having a protrusion. The protrusion aids in the insertion and placement of the implant as well as the spinal fixation element. In certain embodiments the protrusion may be configured as a guide for the insertion of the spinal fixation element as well as closure mechanisms for connecting the spinal fixation element to the implant.

In accordance with a first aspect, an implant is provided for use in a minimally invasive spinal fixation. The implant includes a bone anchor, a connector body and a protrusion. The bone anchor has a proximal head and a distal shaft extending along a longitudinal axis configured to engage bone. The connector body is configured to engage the proximal head of bone anchor and engage a spinal fixation element and includes a cavity for receiving the proximal head of the bone anchor and a seat for receiving the spinal fixation element. The protrusion extends from the connector body along a longitudinal axis opposite and offset of the distal shaft of the bone anchor and defines a stop at one end of the seat.

In certain embodiments, the implant further comprises a cap for connecting a spinal fixation element to the connector body of the implant. The cap is configured to be inserted along the protrusion extending from the connector body. A locking mechanism may further be used to secure the cap and spinal fixation element to the connector body.

In accordance with another aspect, another implant is provided for use in a minimally invasive spinal fixation. The implant includes a bone anchor, a connector body and a detachable post. The bone anchor has a proximal head and a distal shaft extending along a longitudinal axis configured to engage bone. The connector body includes a cavity and a saddle. The cavity is configured to receive the proximal head of the bone anchor. The saddle defines a seat for receiving the spinal fixation element. The detachable post extends from the connector body along a longitudinal axis opposite and offset of the distal shaft of the bone anchor and defines a stop at one end of the seat.

In accordance with another aspect, another implant is provided for use in a minimally invasive spinal fixation. The implant includes a bone anchor, a connector body, and a detachable guide tab. The bone anchor has a proximal head and a distal shaft extending along a longitudinal axis configured to engage bone. The connector body includes a cavity and a saddle. The cavity is configured to receive the proximal head of the bone anchor. The saddle defines a seat for receiving the spinal fixation element. The detachable guide tab extends from the connector body along a longitudinal axis opposite and offset of the distal shaft of the bone anchor and defines a stop at one end of the seat. The detachable guide tab also includes surface configuration for engaging a saddle, a cap, a locking mechanism, and/or an instrument.

BRIEF DESCRIPTION OF THE FIGURES

These and other features and advantages of the devices and methods disclosed herein will be more fully understood by reference to the following detailed description in conjunction with the attached drawings in which like reference numerals refer to like elements through the different views. The drawings illustrate principles of the instruments and methods disclosed herein and, although not to scale, show relative dimensions.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Exemplary embodiments described herein concern implants for securing spinal fixation elements and methods of use. As such, exemplary embodiments of implants may be formed of suitable materials for use in a human body. Suitable materials include, but are not limited to, stainless steel, titanium, PEEK, or the like. Exemplary embodiments of implants are particularly suited for use in rod-first spinal surgical techniques. Exemplary embodiments of implants may be sized and dimensioned for insertion through a minimally invasive surgical access port, such as a cannula.

Figure 1A:
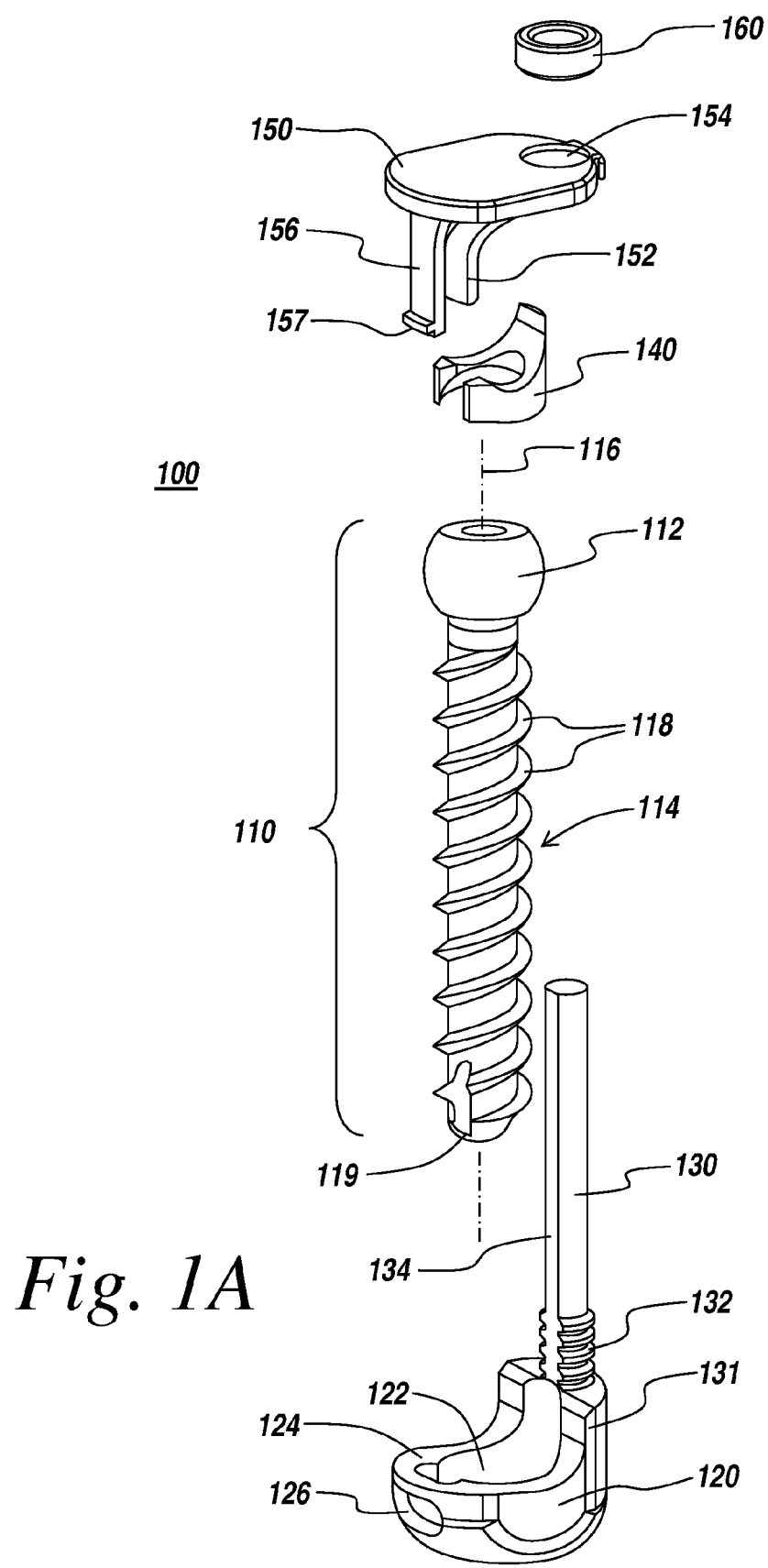
FIG. 1A-B illustrates an exemplary embodiment of an implant.
Figure 1B:
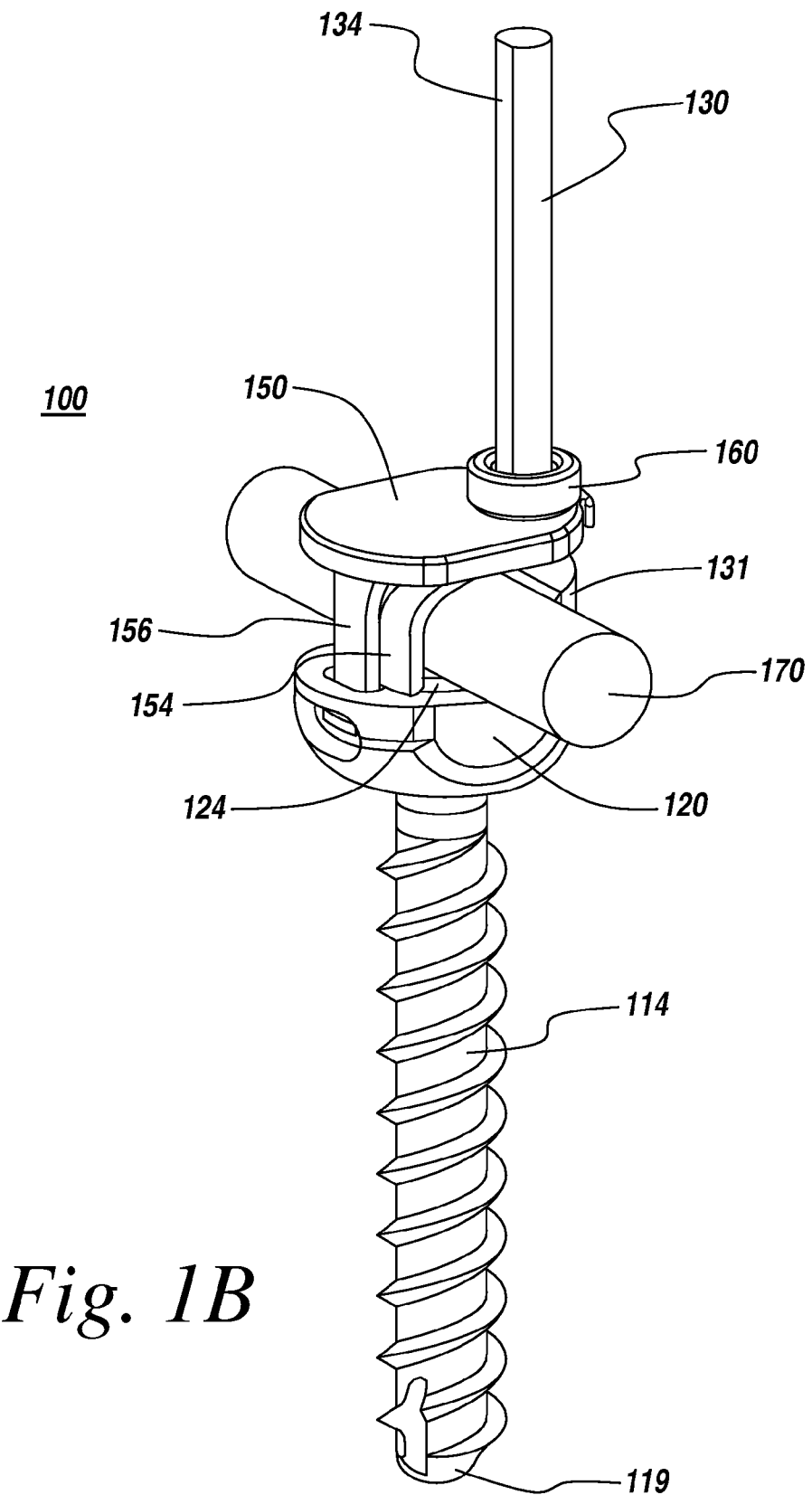

An example of one embodiment of a suitable implant can be seen in FIGS. 1A and 1B. In this example, the implant 100 includes a bone anchor 110, a connector body 120, and a protrusion 130. In certain embodiments a saddle 140, a cap 150, and a locking mechanism 160 may also be included. FIG. 1A depicts a perspective view showing the individual parts of the implant 100. FIG. 1B depicts a perspective view showing the implant 100 assembled.

The bone anchor 110 comprises a connector portion, illustrated as a proximal anchor head 112, for coupling the bone anchor 110 to the connector body 120 and an anchoring portion, illustrated as a distal shaft 114 configured to engage bone. The distal shaft 114 of the bone anchor 110 extends along a longitudinal axis 116. The distal shaft 114 may include one or more bone engagement mechanisms to facilitate gripping engagement of the bone anchor to bone. In the illustrated embodiment, the distal shaft 114 includes an external thread 118 extending along at least a portion of the shaft for engaging bone. In the illustrated embodiment, the external thread 118 is a single lead thread that extends from a distal tip 119 of the shaft to the anchor head 112, though one skilled in the art will recognize that the external thread may extend along any selected portion of the shaft and have any suitable number of leads. Other suitable bone engagement mechanisms include, but are not limited to, one or more annular ridges, multiple threads, single lead threads, variable pitched threads and/or any conventional bone engagement mechanism.

The anchor head 112 of the bone anchor 110 may be configured to facilitate adjustment of the bone anchor 110 relative to the connector body 120 of the implant 110. For example, the illustrative anchor head 112 may be substantially spherical to permit pivoting of the bone anchor 110 relative to the connector body 120 in one or more selected directions. In some embodiments, the anchor head 112 may also have surface texturing, knurling and/or ridges.

In this example, the connector body 120 forms a seat 124 for receiving a spinal fixation element. A cavity 122 passes through the connector body 120 and is configured for receiving the bone anchor 110 and engaging the proximal head 112 of the bone anchor 110.

The connector body 120 receives the proximal head 112 of the bone anchor in the cavity 122 to couple the bone anchor 110 thereto. The connector body 120 receives a spinal fixation element in the seat 124 defined by the connector body 120, thereby coupling the spinal fixation element engaged by the connector body 120 to the bone anchor 110.

The cavity 122 of the connector body 120 is configured to interact with the spherical shape of the proximal head 112 of the bone anchor 110 to allow the bone anchor 110 to rotate and pivot independently of the connecter body 120 and thus provides a polyaxial implant 100. Likewise, once the distal shaft 114 of the bone anchor 110 has been implanted in a bone the interaction of the cavity 122 and proximal head 112 allow the connecter body 120 to be positioned to engage a spinal fixation element 170 as seen in FIG. 1B.

In the example FIGS. 1A and 1B, the protrusion 130 is a post that extends from the connector body 120 in the longitudinal axis 116 opposite and offset of the distal shaft 114 of the bone anchor 110. The protrusion 130 also defines a stop 131 at one end of the seat 124. Having the protrusion 130 offset provides access to the proximal head 112 of the bone anchor 110 for inserting and adjusting the bone anchor 110. Having the protrusion 130 offset and defining a stop 131 at one end of the seat 124 leaves the opposite end open for receiving the spinal fixation device 170. This allows for side and top loading of a spinal fixation element 170 upon the seat 124 while still providing a guide for locating the spinal fixation element 170 along a patient's spine (not shown). Thus, when the spinal fixation device 170 hits the stop 131 defined by the protrusion 130, the user knows the spinal fixation device 170 is properly positioned on the seat 124.

In this example, the protrusion further includes threads 132 for engaging a closure mechanism such as a locking nut 160. In certain embodiments, the protrusion 130 has a break-away feature allowing the protrusion 130 to be detached and removed. Alternatively, the protrusion 130 can be detached by cutting the post away from the implant 100. In still other embodiments, the protrusion 130 may be mechanically attached such as through, a clamp, latch, dovetail, or the like, wherein the protrusion can be detached by disengaging the mechanical attachment. Other possible configurations and techniques will be apparent to one skilled in the art given the benefit of this disclosure.

In some embodiments, the protrusion 130 is configured to extend outside the patient through the patient's skin while providing clear access to the connector body 120 and the proximal head 112 of the bone anchor 110. In other embodiments, the protrusion 130 does not extend outside the patient when inserted. The protrusion 130 may have a number of shapes and configuration allowing for the use of different instruments and closure mechanisms.

In certain embodiments, the protrusion 130 may be bendable, allowing a surgeon to manipulate the protrusion 130 as necessary to fit a particular implementation. In still other embodiments, the protrusion 130 may be radiopaque to assist in placement where direct view of the surgical site is not available.

In certain embodiments, the protrusion 130 may have one or more surface configurations 134 for engaging tools, spinal fixation elements, and/or closure mechanisms to further assist in the insertion and guidance of the tools, spinal fixation elements, and/or closure mechanisms. In the example of FIGS. 1A and 1B, the surface configuration 134 is a flat face on the otherwise cylindrical post 130. The flat face 134 on the post aids in the alignment and insertion of the cap 150.

In the example of FIGS. 1A and 1B, the saddle 140 is provided as part of the implant 100. The saddle 140 is sized and configured to fit inside the cavity 122 in the connector body 120 and define the seat 124. In use, the saddle 140 serves as an interface between proximal head 112 in the cavity 122 of the connector body 120 and a spinal fixation element 170 placed on the seat 124 of the connector body 120. As such the saddle is shaped to mate with the particular geometries of the proximal head 112 and the spinal fixation element 170.

In the examples of FIGS. 1A and 1B, a closure mechanism in the form of the cap 150 is also provided. The cap 150 is configured to capture a spinal fixation element 170 on the saddle 140 defining the seat 124 of the connector body. The cap 150 includes a hook 152, a pass-through hole 154, and a snap-fit feature 156.

The hook 152 is configured to capture and hold the spinal fixation element 170 on the seat 124 of the connector body thereby connecting the spinal fixation element 170 to the implant 100. An example of this can be seen in FIG. 1B. The pass-through hole 154 allows the cap 150 to be inserted over post 130 of the implant 100. In the present example, the pass-through hole 154 is keyed to match the flat side 134 of the post 130. Thus the post 130 acts as a guide for the insertion of the cap 150.

The snap-fit feature 156 serves to interlock the cap 150 with the connector body 120. In this embodiment, the snap-fit feature 156 of the cap 150 includes a deformable finger having surface configurations 157. When mated with the connector body 120, the surface configurations 157 engage interlocking surface configurations 126 on the connector body 120 providing a snap fit. The snap-fit feature 156 also provides audible and tactile feedback that the cap 150 has captured the spinal fixation element 170 and mated with the connector body 120.

A locking mechanism 160 may also be provided to secure the connection of the spinal fixation element 170 to the implant 100. In the present example, the locking mechanism 160 is a locking nut configured to engage the threads 132 of the post 130 and secure the cap 150 and spinal fixation element 170 to the connector body 120. An example of this can be seen in FIG. 1B.

In use, the connector body 120 may be placed at a surgical site with the protrusion extending outside of the patient. In certain embodiments, the posts 130 may be used in the placement of the connector body 120 at the surgical site. The bone anchor 110 may then be inserted through the cavity 122 of the connector body into a vertebra (not shown) at the surgical site. The bone anchor 110 serves to connect the connector body 120 to the vertebra. The saddle 140 may then be placed onto the proximal head 112 of the bone anchor in the cavity 122 of the connector body 120. In certain embodiments, the implant 100 including the bone anchor 110, connector body, and saddle 140 may be pre-assembled before insertion and placement at a surgical side. In such embodiments, the saddle 140 may be configured to allow access to the proximal head 112 of the bone anchor 110 after the saddle 140 has been inserted to allow for adjustment to the bone anchor 110.

Once the implant 100, including the bone anchor 110, connector body 120, and post 130, are in place, a spinal fixation element 170 may be placed on the seat 124. The spinal fixation element 170 may be inserted before or after the implant 100 and then placed on the seat 124. In certain embodiments, the spinal fixation element may be inserted through the same incision used to insert the implant 100. In many instances, the implant, as well as the spinal fixation element 170, are inserted using minimally invasive surgical techniques. When using minimally invasive surgical techniques, visibility of the surgical site may be limited. Thus the post 130 extending out of the patient may provide a useful visual indicator for the position of the implant 100. As discussed previously, the post 130 is offset providing access to the proximal head 112 of the bone anchor 110 for inserting and adjusting the bone anchor 110. The protrusion 130 also defines a stop 131 at one end of the seat 124. Having the protrusion 130 offset provides access to the proximal head 112 of the bone anchor 110 for inserting and adjusting the bone anchor 110. Having the protrusion 130 offset and defining a stop 131 on the seat 124 also allows for side and top loading of a spinal fixation element 170 upon the seat 124 while still providing a guide for locating the spinal fixation element 170 along a patient's spine (not shown). Thus, when the spinal fixation device 170 hits the stop 131 defined by the protrusion 130, the user knows the spinal fixation device 170 is properly positioned on the seat 124.

Once the spinal fixation element 170 has been seated on the implant 100, the cap 150 may be inserted to capture and retain the spinal fixation element 170 on the implant 100. Again, the post 130 extending outside the patient may serve as a guide for the insertion of the cap 150. The cap 150 is placed over the post 130, wherein the post 130 passes through the pass-through hole 154 of the cap, and slid along the length of the post 130 to the surgical site. As mentioned above, the pass-through hole 154 of the cap 150 is keyed to the surface configurations 134 of the post 130 so there is only one possible orientation for insertion. Once at the surgical site, the hook 152 of the cap 150 captures and retains the spinal fixation element 170 on the seat 124 of the connector body 120. When the cap 150 is mated to connector body 120, the surface configurations 157 of the deformable finger of the snap-fit feature 156 engages the matching configuration 126 on the connector body 120 to provide a snap-fit connection as well as audible and tactile feedback to the surgeon.

Although the spinal fixation element 170 may be captured on the seat 124 of the connector body 120 by the cap 150, the spinal fixation element 170 may still be movable on the seat 124. Likewise, as discussed above, the connector body 120 is pivotable on the proximal head 112 of the bone anchor 110. Hence, the locking nut 160 is provided to secure the position of the spinal fixation element 170 and connector body 120. Once the spinal fixation element 170 has been captured by mating the cap 150 to the connector body 120, the locking nut 160 may be inserted over and slid along the length of the post 130 to the surgical site. Locking nut 160 may then engage the threads 132 on the post. When the locking nut 160 is tightened, the locking nut 160 pushes against the cap 150 which in turn pushes against and engages the spinal fixation element 170. The spinal fixation element 170 pushes against the saddle 140 sitting in the cavity 122 of the connector body 120, which, in turn, pushes against and engages the proximal head 112 of the bone anchor 110 passing through the cavity 122 of the connector body 120. As such, the tightening of the locking nut 160 secures the position of the spinal fixation element 170 and the connector body. In other embodiment the cap 150 could serve to secure position of the spinal fixation element 170 without the need of a locking mechanism 160.

Once the position of spinal fixation element 170 and connector body 120 have been secured, the post 130 may be removed. As discussed previously, the post 130 may have a break-away feature allowing the post 130 to be detached and removed. In still other embodiments, the post 130 may be mechanically attached such as through, a clamp, latch, dovetail, or the like, wherein the post 130 can be detached by disengaging the mechanical attachment. Alternatively, the post 130 can be detached by cutting the post 130 away from the implant 100.

Figure 2A:
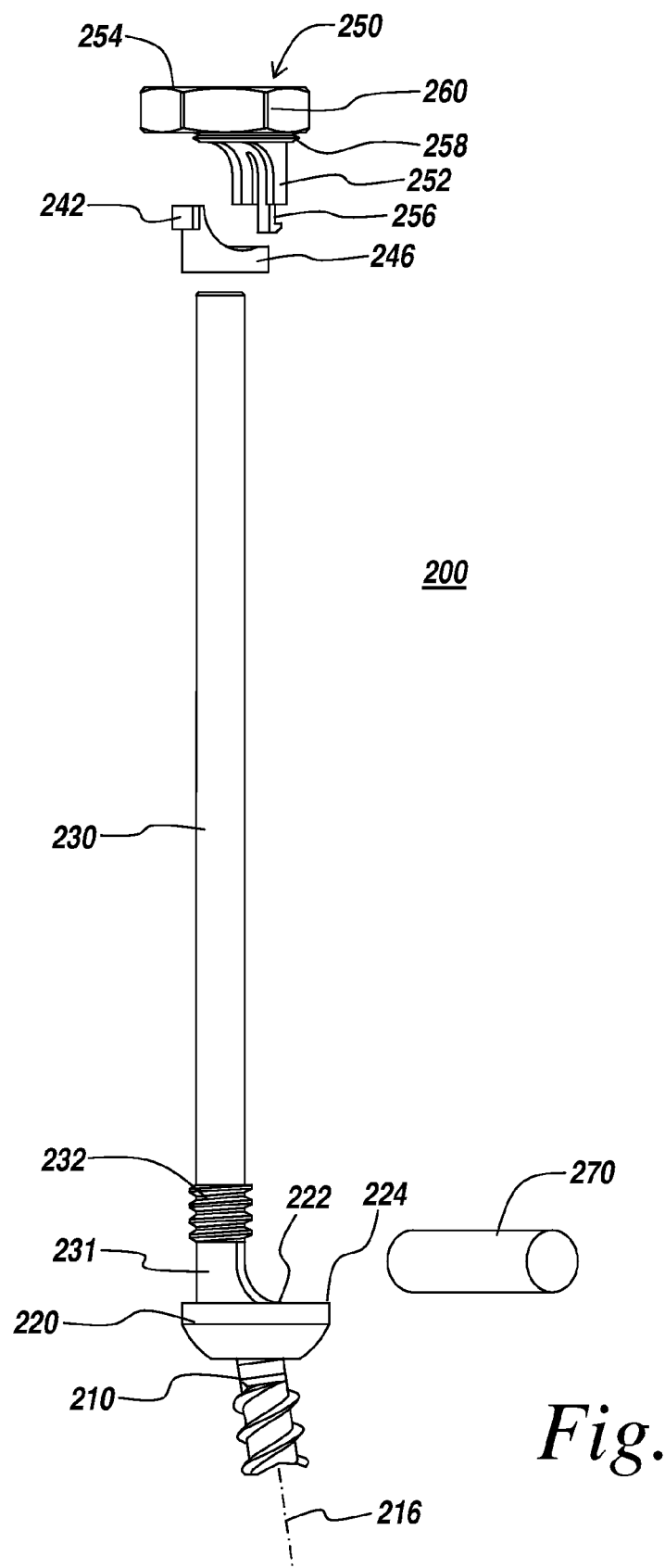
FIGS. 2A-2B illustrate another exemplary embodiment of an implant.
Figure 2B:
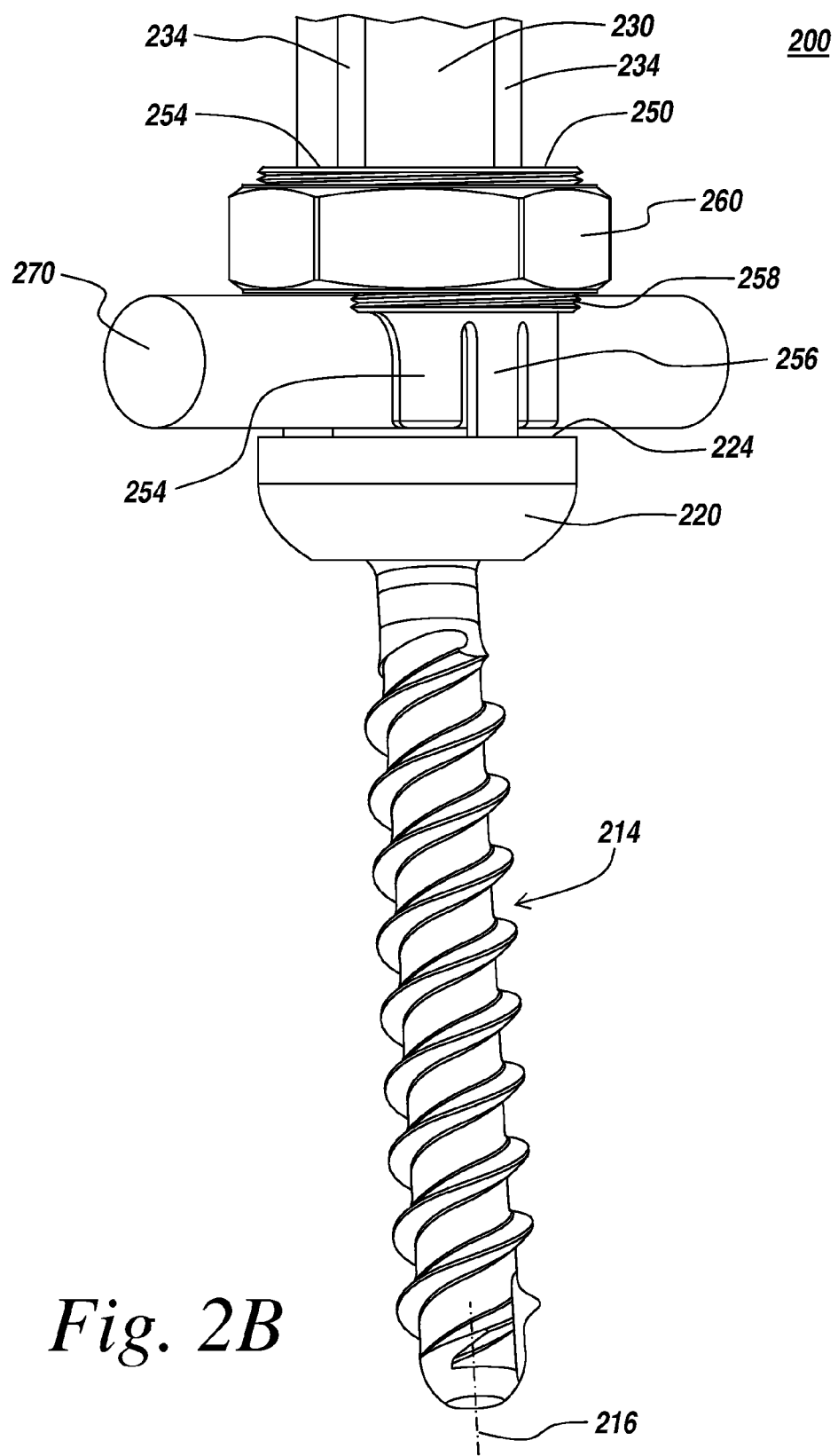

FIGS. 2A and 2B depict another embodiment of an implant 200 for securing a spinal fixation element. FIG. 2A depicts an exploded view of the implant 200. FIG. 2B depicts the implant 200 assembled and engaging a spinal fixation element 270, in this case a spinal rod.

In the embodiment of FIGS. 2A and 2B, the implant 200 has a bone anchor 210, a connector body 220, and a protrusion 230. In the example depicted in FIGS. 2A and 2B, the bone anchor 210 and connector body 220 are already assembled such that the proximal head (not shown) of the bone anchor 210 is engaged by the cavity 222 of the connector body 220, leaving only the distal shaft 214 of the bone anchor 210 visible. The implant 200 also includes a saddle 240, and a locking cap 250.

In this example, the protrusion 230 is a guide tab that extends from the connector body 220 in the longitudinal axis 216 opposite and offset of the distal shaft 214 of the bone anchor 210 and defines a stop 231 at one end of the seat 224. The guide tab 230 is configured to extend outside the patient through the patient's skin while providing clear access to the connector body 220 and the proximal head of the bone anchor 210. Accordingly, the guide tab 230 may form a partial cannula extending through the skin wherein the guide tab has a crescent shaped cross section.

The guide tab includes threads 232 for engaging a closure mechanism such as a locking cap 250. In certain embodiments, the guide tab 230 has a break-away feature allowing the guide tab 230 to be detached and removed. In still other embodiments, the guide tab 230 may be mechanically attached such as through, a clamp, latch, dovetail, or the like, wherein the guide tab 230 can be detached by disengaging the mechanical attachment. Alternatively, the guide tab 230 can be detached by cutting the post away from the implant 200. Other possible configurations and techniques will be apparent to one skilled in the art given the benefit of this disclosure.

In certain embodiments, the guide tab 230 may have one or more surface configurations 234 for engaging tools, spinal fixation elements, and/or closure mechanisms to further assist in the insertion and guidance of the tools, spinal fixation elements, and/or closure mechanisms. In the example of FIGS. 2A and 2B, the surface configuration 234 include a dovetail feature that mates with the saddle 240 and locking cap 250.

In the example of FIGS. 2A and 2B, a saddle 240 is provided as part of the implant 200. The saddle 240 is sized and configured to fit inside the cavity 222 in the connector body 220 and define the seat 224. In this embodiment, the saddle 240 further includes surface configurations 242 for mating with the dovetail feature 234 of the guide tab 230.

In the examples of FIGS. 2A and 2B, a closure mechanism in the form of a locking cap 250 is also provided. The locking cap 250 is configured to capture a spinal fixation element 270 on the saddle 240 defining the seat 224 of the connector body 220. The locking cap 250 includes a hook 252, a pass-through hole 254, a snap-fit feature 256, and an integrated locking nut 260.

The hook 252 is configured to capture and hold the spinal fixation element 270 on the seat 224 of the connector body thereby connecting the spinal fixation element 270 to the implant 100. An example of this can be seen in FIG. 2B. The hook 252 also has external threads 258 for engaging the integrated locking nut 260. The pass-through hole 254 allows the locking cap 250 to be inserted over guide tab 230 of the implant 200. Thus the guide tab 230 serves to guide the locking cap 250 during insertion. The snap-fit feature 256 serves to interlock the locking cap 250 with the connector body 220. The snap-fit feature 256 also provides audible and tactile feedback that the locking cap 250 has captured the spinal fixation element 270 and mated with the connector body 220.

The locking cap 250 also includes an integrated locking nut 260. The integrated locking nut 260 is configured to engage the threads 232 of the guide tab 230 and the threads 258 of the hook 252 and secure the locking cap 250 and spinal fixation element 270 to the connector body 220. An example of this can be seen in FIG. 2B.

In use, the connector body 220 may be placed at a surgical site with the protrusion extending outside of the patient. In certain embodiments, the guide tab 230 may be used in the placement of the connector body 220 at the surgical site. The bone anchor 210 may then be inserted through the cavity 222 of the connector body into a vertebra (not shown) at the surgical site. The bone anchor 210 thus serves to connect the connector body 220 to the vertebra. The saddle 240 may then be placed onto the proximal head (not shown) of the bone anchor in the cavity 222 of the connector body 220. The saddle 240 includes surface configurations 242 designed to mate with the dovetail configurations 234 on the guide tab 230 allowing the guide tab 230 to be used as guide that the saddle 240 may be slide along the length of for insertion. In other embodiments, the implant 200 including the bone anchor 210, connector body, and saddle 240 may be pre-assembled before insertion and placement at a surgical side. The saddle 240 may be configured to allow access to the proximal head (not shown) of the bone anchor 210 after the saddle 240 has been inserted to allow for adjustment to the bone anchor 210.

Once the implant 200, including the bone anchor 210, connector body 220, and guide tab 230 are in place, a spinal fixation element 270 may be placed on the seat 224. The spinal fixation element 270 may be inserted before or after the implant 200 and then placed on the seat 224. In certain embodiments, the spinal fixation element 270 may be inserted through the same incision used to insert the implant 200. In many instances, the implant, as well as the spinal fixation element 270, is inserted using minimally invasive surgical techniques. When using minimally invasive surgical techniques, visibility of the surgical site maybe limited. Thus the guide tab 230 extending out of the patient may provide a useful visual indicator for the position of the implant 200. The guide tab 230 may also serve as a physical guide for the placement of the spinal fixation element 270 on the seat 224 of the implant 200. As previously discussed, the protrusion 230 also defines a stop 231 at one end of the seat 224. Thus, when the spinal fixation device 270 hits the stop 231 defined by the protrusion 230, the user knows the spinal fixation device 270 is properly positioned on the seat 224.

Once the spinal fixation element 270 has been seated on the implant 200, the locking cap 250 may be inserted to capture, retain, and secure the spinal fixation element 270 on the implant 200. The guide tab 230 extending outside the patient may serve as a guide for the insertion of the locking cap 250. The locking cap 250 is placed over the guide tab 230, wherein the guide tab 230 passes through the pass-through hole 254 of the cap, and slid along the length of the guide tab 230 to the surgical site. Once at the surgical site, the hook 252 of the locking cap 250 captures and retains the spinal fixation element 270 on the seat 224 of the connector body 220. When the cap 250 is mated to the connector body 220, the surface configurations 257 of the deformable finger of the snap-fit feature 256 is deflected by the saddle 240 and locked into a matching configuration (not shown) on the connector body 220 to provide a snap-fit connection as well as audible and tactile feedback to the surgeon.

The integrated locking nut 260 is provided to secure the locking cap 250 and the position of the spinal fixation element 270 and connector body 220. Once the spinal fixation element 270 has been captured by mating the locking cap 250 to the connector body 220, the integrated locking nut 260 may be tightened. When the integrated locking nut 260 is tightened, the integrated locking nut 260 pushes against the spinal fixation element 270. The spinal fixation element 270 pushes against the saddle 240 sitting in the cavity 222 of the connector body 220 which in turn pushes against and engages the proximal head (not shown) of the bone anchor 210 passing through the cavity 222 of the connector body 220. Thus, by tightening the integrated locking nut 260 the locking cap 250 as well as the positions of the spinal fixation element 270 and the connector body are secured.

Once the position of spinal fixation element 270 and connector body 220 have been secured using the integrated locking nut 260, the guide tab 230 may then be removed. As discussed previously, the guide tab 230 may have a break-away feature allowing the guide tab 230 to be detached and removed. Alternatively, the guide tab 230 can be detached by cutting the guide tab 230 away from the implant 200. In still other embodiments, the protrusion 230 may be mechanically attached such as through, a clamp, latch, dovetail, or the like, wherein the protrusion can be detached by disengaging the mechanical attachment. Other possible implementations and embodiments will be apparent to one skilled in the art given the benefit of this disclosure.

Figure 3A:
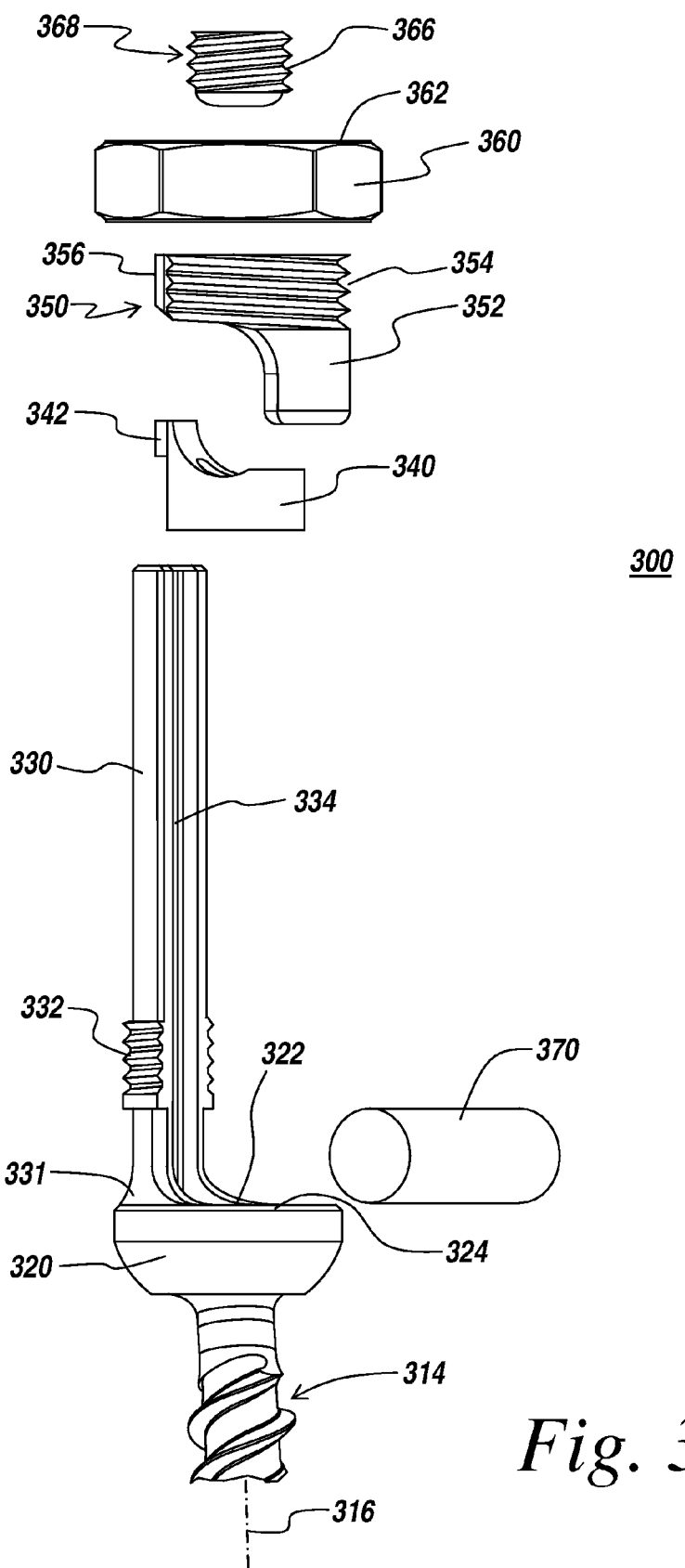
FIGS. 3A-3C illustrate another exemplary embodiment of an implant.
Figure 3B:
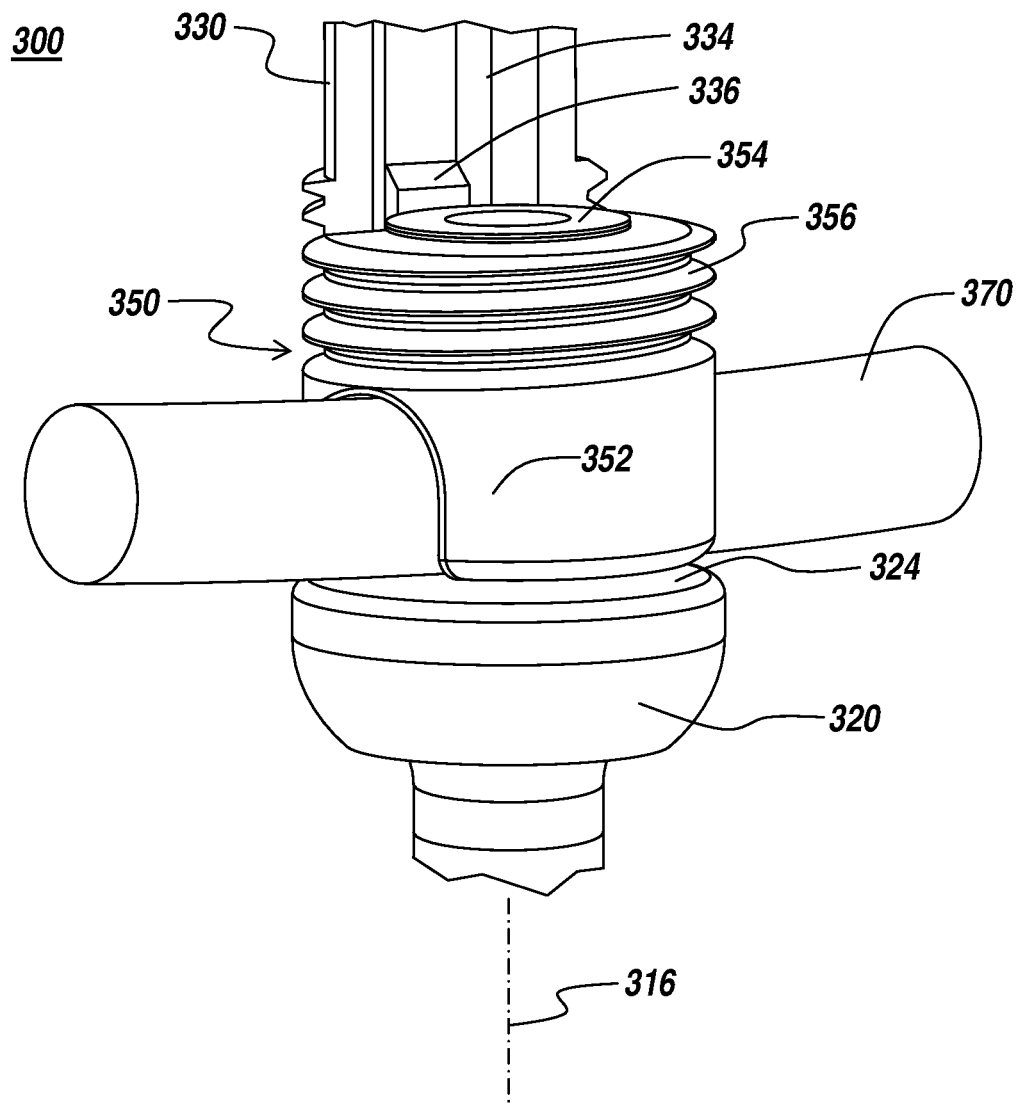
Figure 3C:
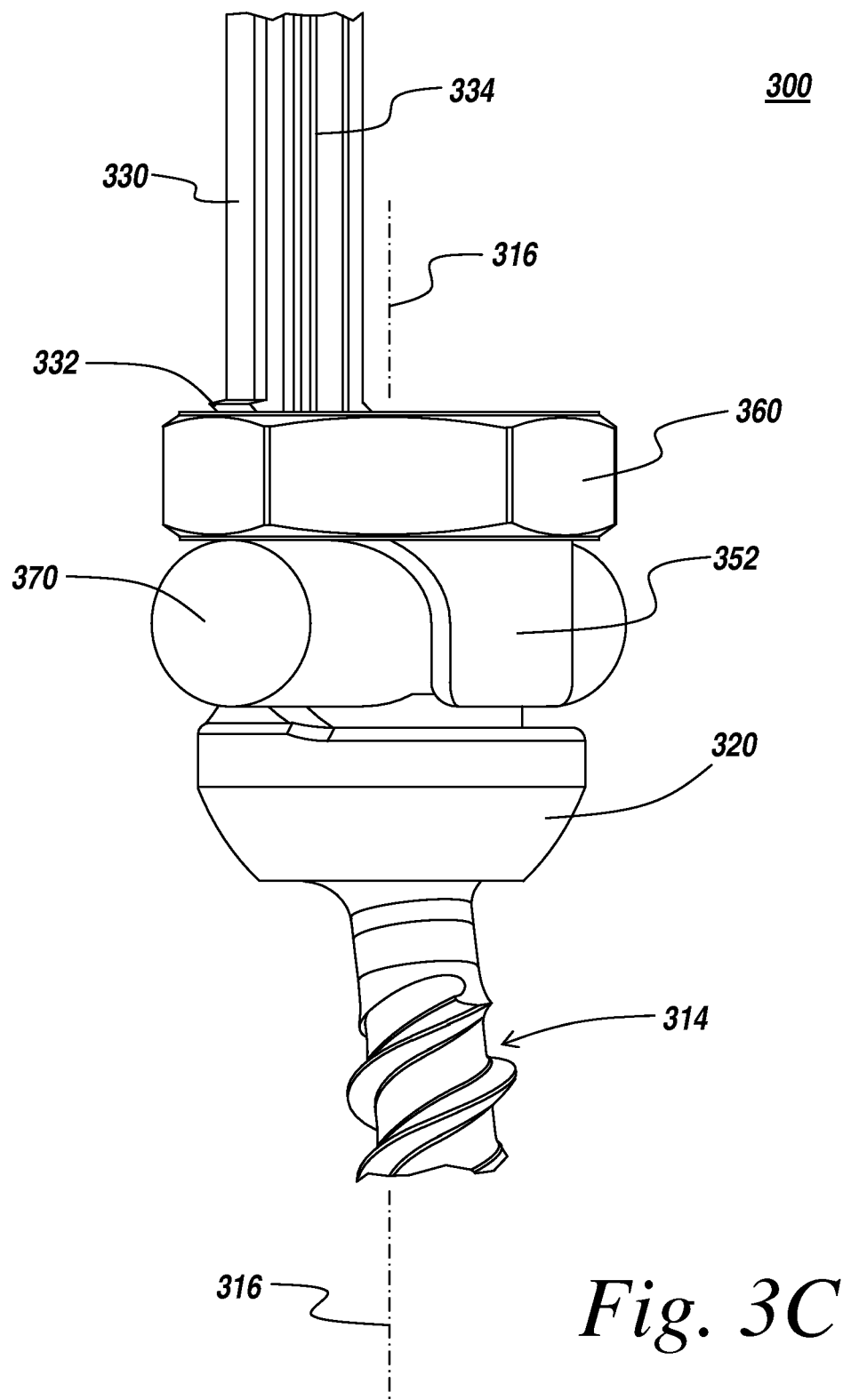

Another embodiment of an implant 300 can be seen in FIGS. 3A-3C. In this embodiment the implant 300 has a bone anchor 310, a connector body 320, and protrusion 330. As with FIGS. 2A and 2B, the bone anchor 310 and connector body 320 are already assembled such that the proximal head (not shown) of the bone anchor 310 is engaged by the cavity 322 of the connector body 320. In this embodiment, the implant 300 further includes a saddle 340, a cap 350, a first locking mechanism 360 and a second locking mechanism 366.

In this example, the protrusion 330 is a guide tab that extends from the connector body 320 in the longitudinal axis 316 opposite and offset of the distal shaft 314 of the bone anchor 310 and defining a stop 331 at one end of the seat 324. The guide tab 330 is configured to extend outside the patient through the patient's skin while providing clear access to the connector body 320 and the proximal head (not shown) of the bone anchor 310. Accordingly, the guide tab 330 may form a partial cannula extending through the skin wherein the guide tab has a crescent shaped cross section.

The guide tab includes threads 332 for engaging a closure mechanism such as a cap 350. In certain embodiments, the guide tab 330 has a break-away feature allowing the guide tab 230 to be detached and removed. In still other embodiments, the guide tab 330 may be mechanically attached such as through, a clamp, latch, dovetail, or the like, wherein the guide tab 330 can be detached by disengaging the mechanical attachment. Alternatively, the guide tab 330 can be detached by cutting the post away from the implant 300. Other possible configurations and techniques will be apparent to one skilled in the art given the benefit of this disclosure.

In certain embodiments, the guide tab 330 may have one or surface configurations 334 for engaging tools, spinal fixation elements, and/or closure mechanisms to further assist in the insertion and guidance of the tools, spinal fixation elements, and/or closure mechanisms. In the example of FIG. 3A-3C, the surface configuration 334 include a dovetail feature that mates with the saddle 340 and cap 350.

In the example of FIGS. 3A-3C, a saddle 340 is provided as part of the implant 300. The saddle 340 is sized and configured to fit inside the cavity 322 in the connector body 320 and define the seat 324. In this embodiment, the saddle 340 further includes surface configurations 342 for mating with the dovetail feature 334 of the guide tab 330.

In the examples of FIGS. 3A-3C, a closure mechanism in the form of a cap 350 is also provided. The cap 350 is configured to capture a spinal fixation element 370 on the saddle 340 defining the seat 324 of the connector body 320. The cap 350 includes a hook 352, a threaded passage 354, external threads 356, and one or more surface configurations 358.

The hook 352 is configured to capture and hold the spinal fixation element 370 on the seat 324 of the connector body thereby connecting the spinal fixation element 370 to the implant 300. An example of this can be seen in FIG. 3B. The threaded passage 354 is configured to receive the second locking mechanism 366. The external threads 356 are configured to engage the first locking mechanism 360. The surface configurations 358 are for mating with the dovetail feature 334 of the guide tab 330.

The first locking mechanism 360 is a locking nut. The first locking mechanism 360 is configured to be placed over the guide tab 330 and cap 350 engaging the threads 332 of the guide tab 330 and the external threads 356 of the cap 350 to secure the cap 350 and spinal fixation element 370 to the connector body 320. An example of this can be seen in FIG. 3C.

The second locking mechanism 366 is a set screw having external threads 368. The second locking mechanism 366 is configured to be inserted into the threaded passage 354 of the cap 350 engaging the threads of the threaded passage 354 of the cap 350 with external threads 368 to secure the spinal fixation element 370.

In use, the connector body 320 may be placed at a surgical site with the protrusion extending outside of the patient. In certain embodiments, the guide tab 330 may be used in the placement of the connector body 320 at the surgical site. The bone anchor 310 may then be inserted through the cavity 322 of the connector body into a vertebra (not shown) at the surgical site. The bone anchor 310 thus serves to connect the connector body 320 to the vertebra. The saddle 340 may then be placed onto the proximal head (not shown) of the bone anchor in the cavity 322 of the connector body 320. The saddle 340 includes surface configurations 342 designed to mate with the dovetail features 334 on the guide tab 330 allowing the guide tab 330 to be used as guide that the saddle 340 may be slide along the length of for insertion. In other embodiments, the implant 300 including the bone anchor 310, connector body, and saddle 340 may be pre-assembled before insertion and placement at a surgical side. The saddle 340 may be configured to allow access to the proximal head (not shown) of the bone anchor 310 after the saddle 340 has been inserted to allow for adjustment to the bone anchor 310.

Once the implant 300, including the bone anchor 310, connector body 320, and guide tab 330 are in place, a spinal fixation element 370 may be placed on the seat 324. The spinal fixation element 370 may be inserted before or after the implant 300 and then placed on the seat 324. In certain embodiments, the spinal fixation element may be inserted through the same incision used to insert the implant 300. In many instances, the implant, as well as the spinal fixation element 370, is inserted using minimally invasive surgical techniques. When using minimally invasive surgical techniques, visibility of the surgical site maybe limited. Thus the guide tab 330 extending out of the patient may provide a useful visual indicator for the position of the implant 300. The guide tab 330 may also serve as a physical guide for the placement of the spinal fixation element 370 on the seat 324 of the implant 300. As previously discussed, the guide tab 330 also defines a stop 331 at one end of the seat 324. Thus, when the spinal fixation device 370 hits the stop 331 defined by the guide tab 330, the user knows the spinal fixation device 370 is properly positioned on the seat 324.

Once the spinal fixation element 370 has been seated on the implant 300, the cap 350 may be inserted to capture and retain the spinal fixation element 370 on the implant 300. The guide tab 330 extending outside the patient may serve as a guide for the insertion of the cap 350. The cap 350 has surface configurations 358 that mate with the dovetail feature 334 of the guide tab 330 which hold the cap 350 in the correct orientation while the cap 350 is slid along the length of the guide tab 330 for insertion. Once at the surgical site, the hook 352 of the cap 350 captures and retains the spinal fixation element 370 on the seat 324 of the connector body 320. The cap 350 may further be locked in place using a surface configuration 336 in the dovetail feature 334, such as locking tooth, that provide a snap-fit. An example of this can be seen in FIG. 3B.

The first locking mechanism 360 is provided to secure the cap 350 and the position of the spinal fixation element 370 and connector body 320. Once the spinal fixation element 370 has been captured, the first locking mechanism 360 may be inserted over the guide tab 330 and cap 350 to engage the threads 332 on the guide tab 330 and the external threads 356 on the cap 350. When the first locking mechanism 360 is tightened, the first locking mechanism 360 pushes against the spinal fixation element 370. The spinal fixation element 370 pushes against the saddle 340 sitting in the cavity 322 of the connector body 320 which in turn pushes against and engages the proximal head (not shown) of the bone anchor 310 passing through the cavity 322 of the connector body 320. Thus, by tightening the first locking mechanism 360, the locking cap 360, as well as the positions of the spinal fixation element 370 and the connector body 320, is secured. An example of this can be seen in FIG. 3C.

In the example of FIGS. 3A-3C, the implant 300 is further provided with a second locking mechanism 366 in the form of a set screw. The second locking mechanism 366 may be used to further secure the position of the spinal fixation element 370 and the connector body 320. The second locking mechanism 366 is configured to be inserted through the threaded passage 354 of the cap 350 to engage the spinal fixation element 370. In certain embodiments, the second locking mechanism 366 may be pre-loaded in the cap 350 when the cap 350 is inserted. When the second locking mechanism 366 is tightened, the second locking mechanism 366 pushes against and engages the spinal fixation element 370. The spinal fixation element 370 pushes against the saddle 340 sitting in the cavity 322 of the connector body 320 which in turn pushes against and engages the proximal head (not shown) of the bone anchor 310 passing through the cavity 322 of the connector body 320. Thus, by tightening the second locking mechanism 366, the positions of the spinal fixation element 370 and the connector body 320 are secured.

Once the position of spinal fixation element 370 and connector body 320 have been secured using the first locking mechanism 360 and second locking mechanism 366, the guide tab 330 may then be removed. As discussed previously, the guide tab 330 may have a break-away feature allowing the guide tab 330 to be detached and removed. In still other embodiments, the guide tab 330 may be mechanically attached such as through, a clamp, latch, dovetail, or the like, wherein the guide tab can be detached by disengaging the mechanical attachment. Alternatively, the guide tab 330 can be detached by cutting the guide tab 330 away from the implant 300. Other possible implementations and embodiments will be apparent to one skilled in the art given the benefit of this disclosure.

Another embodiment of an implant 400 can be seen in FIGS. 4A-4F. As with the previous embodiments, in this embodiment the implant 400 has a bone anchor 410, a connector body 420, and protrusion 430. In this embodiment, the implant 400 further includes a saddle 440, a cap 450, and a locking mechanism 460.

In this example, the protrusion 430 is a guide tab that extends from the connector body 420 in the longitudinal axis 416 opposite and offset of the distal shaft 414 of the bone anchor 410 and defines a stop 431 at one end of the seat 424. The guide tab 430 is configured to extend outside the patient through the patient's skin while providing clear access to the connector body 420 and the proximal head 412 of the bone anchor 410. Accordingly, the guide tab 430 may form a partial cannula extending through the skin wherein the guide tab has a crescent shaped cross section.

In certain embodiments, the guide tab 430 has a break-away feature allowing the guide tab 430 to be detached and removed. Alternatively, the guide tab 430 can be detached by cutting the post away from the implant 400. In still other embodiments, the protrusion 330 may be mechanically attached such as through, a clamp, latch, dovetail, or the like, wherein the protrusion can be detached by disengaging the mechanical attachment. Other possible configurations and techniques will be apparent to one skilled in the art given the benefit of this disclosure.

In certain embodiments, the guide tab 430 may have one or surface configurations 434 for engaging tools, spinal fixation elements, and/or closure mechanisms to further assist in the insertion and guidance of the tools, spinal fixation elements, and/or closure mechanisms. In the example of FIG. 4A-4F, the surface configurations 434 include tracks that mate with the cap 450 and guide the insertion of the cap 450. In this embodiment, the guide tab 430 further includes a relief section 432 wherein the cap 450 may be disengaged from the tracks 434 of the guide tab 430 to mate cap 450 with the connector body 420 which will be discussed in more detail below.

In the example of FIGS. 4A-4F, a saddle 440 is provided as part of the implant 400. The saddle 440 is sized and configured to fit inside the cavity 422 in the connector body 420 and define the seat 424.

In the examples of FIGS. 4A-4F, a closure mechanism 450 in the form of a cap is also provided. The cap 450 is configured to capture a spinal fixation element 470 on the saddle 440 defining the seat 424 of the connector body 420. The cap 450 includes a hook 452, a threaded passage 454, a sliding lock feature 456, and surface configuration 458 for engaging the tracks 434 of the guide tab 430.

The hook 452 is configured to capture and hold the spinal fixation element 470 on the seat 424 of the connector body thereby connecting the spinal fixation element 470 to the implant 400. The threaded passage 454 is configured to receive the locking mechanism 460. The sliding lock feature 456 is configured to slidably engage matching features 426 on the connector body 420. This is discussed in more detail in regard to FIGS. 4c-4F. The surface configurations 458 are for mating with the tracks 434 of the guide tab 430.

The locking mechanism 460 is a set screw. The set screw 460 is configured to be inserted into the threaded passage 454 of the cap 450 engaging the threads of the threaded passage 454 of the cap 450 to secure the spinal fixation element 470.

In use, the implant 400 may be placed at a surgical site with the protrusion extending outside of the patient. In certain embodiments, the guide tab 430 may be used in the placement of the implant at the surgical site. In this example, the implant 400 including the bone anchor 410, connector body 420, and saddle 440 are pre-assembled before insertion and placement at a surgical side. As such, the saddle 440 is configured to allow access to the proximal head 414 of the bone anchor 410 after the saddle 440 has been inserted to allow for adjustment to the bone anchor 410.

Once the implant 400, including the bone anchor 410, connector body 420, and guide tab 430 are in place, a spinal fixation element 470 may be placed on the seat 424. The spinal fixation element 470 may be inserted before or after the implant 400 and then placed on the seat 424. In certain embodiments, the spinal fixation element may be inserted through the same incision used to insert the implant 400. In many instances, the implant, as well as the spinal fixation element 470, is inserted using minimally invasive surgical techniques. When using minimally invasive surgical techniques, visibility of the surgical site maybe limited. Thus the guide tab 430 extending out of the patient may provide a useful visual indicator for the position of the implant 400. The guide tab 430 may also serve as a physical guide for the placement of the spinal fixation element 470 on the seat 424 of the implant 400. As previously discussed, the guide tab 430 also defines a stop 431 at one end of the seat 424. Thus, when the spinal fixation device 470 hits the stop 431 defined by the guide tab 430, the user knows the spinal fixation device 470 is properly positioned on the seat 424.

Once the spinal fixation element 470 has been seated on the implant 400, the cap 450 may be inserted to capture and retain the spinal fixation element 470 on the implant 400. The guide tab 430 extending outside the patient may serve as a guide for the insertion of the cap 450. The cap 450 has surface configurations 458 that mate with the tracks 434 of the guide tab 430 which hold the cap 450 in the correct orientation while the cap 450 is slid along the length of the guide tab 430 for insertion. Once at the surgical site, the hook 452 of the cap 450 captures and retains the spinal fixation element 470 on the seat 424 of the connector body 420. An example of this can be seen in FIG. 4C.

Figure 4A:
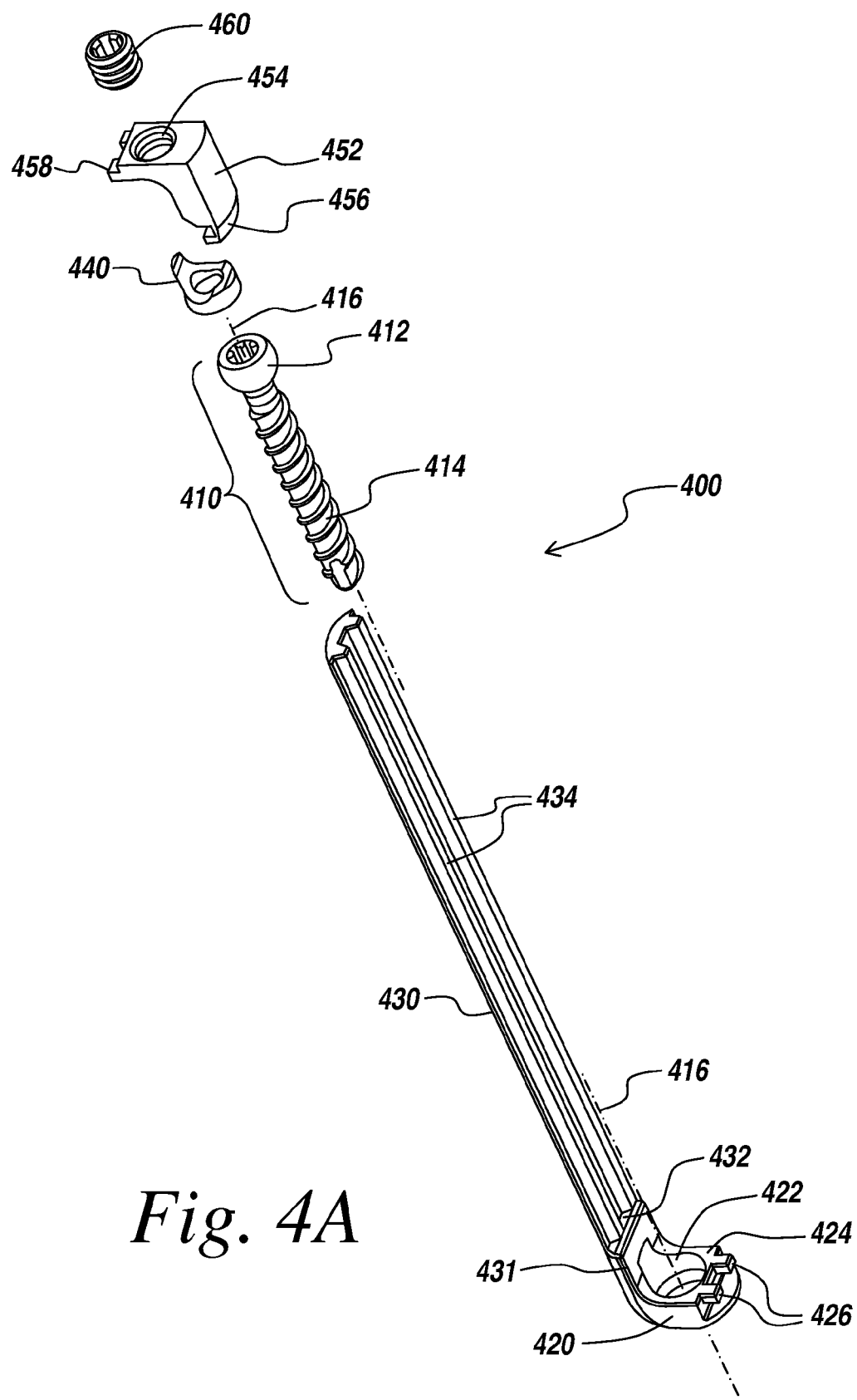
FIGS. 4A-4F illustrate another exemplary embodiment of an implant.
Figure 4B:
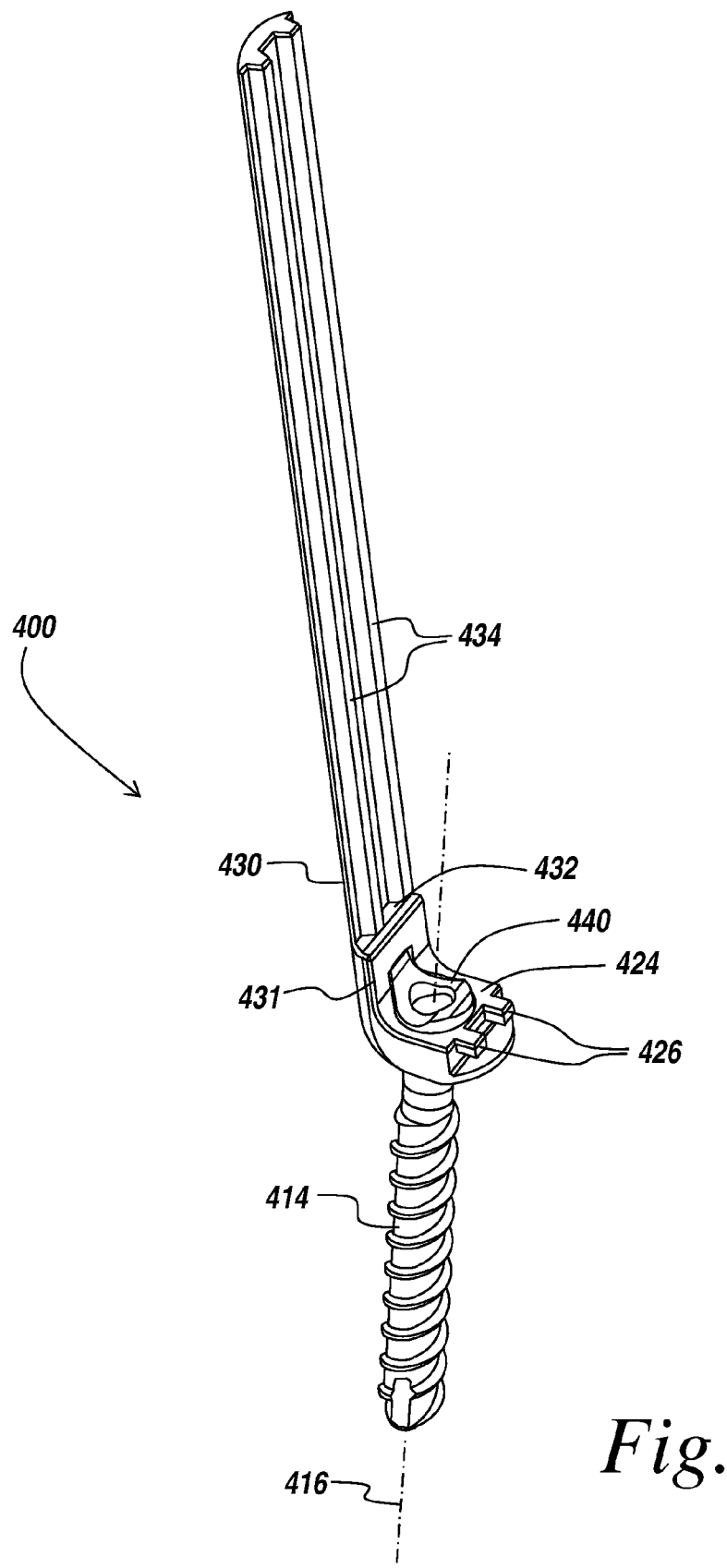
Figure 4C:
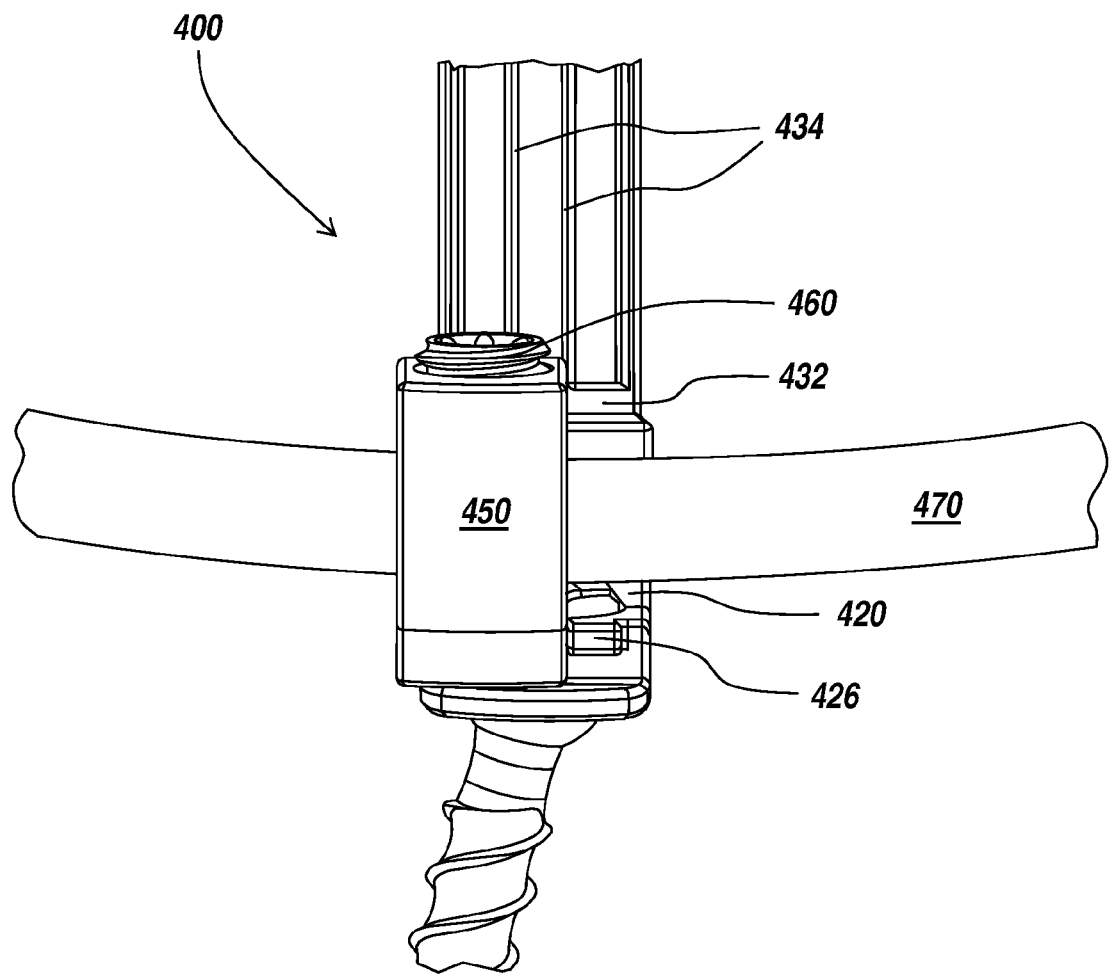
Figure 4D:
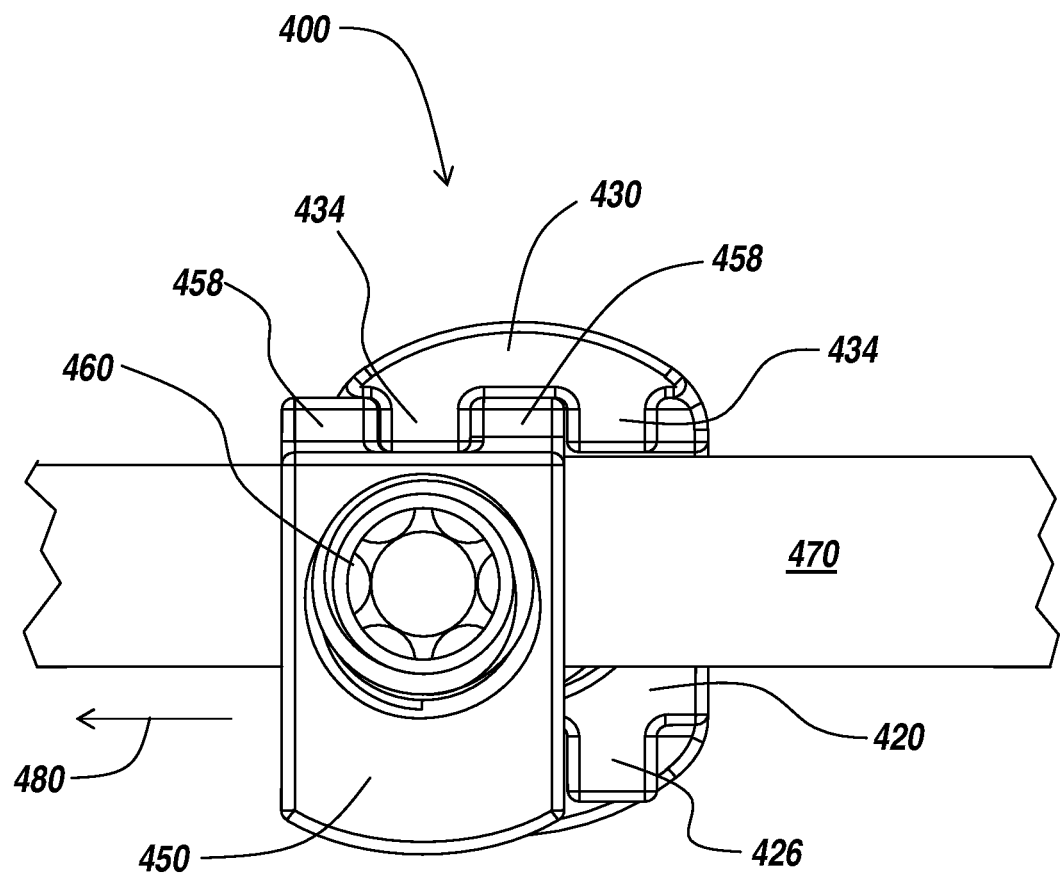

As can be seen in FIGS. 4C and 4D, the cap 450 is mated with one of the tracks 434 of the guide tab 430 as it slide along the length of the guide tab 430 to the surgical site to capture the spinal fixation element 470. This means that the cap 450 is laterally offset from the connector body 420 when cap 450 reaches the implant site. However, in this example, the cap 450 is provided with a sliding lock feature 456 to slidably mate with the connector body 420 to secure the spinal fixation element 470. As previously mentioned, the guide tab 430 is provided with a relief section 432 proximal to connector body 420 which allows the cap 450 to disengage the tracks 434 of the guide tab 430. Thus, when the cap 450 has captured the spinal fixation element 470 at the implant site, the cap 450 may be slid laterally to engage the connector body 420 shown in FIGS. 4E and 4F.

Figure 4E:
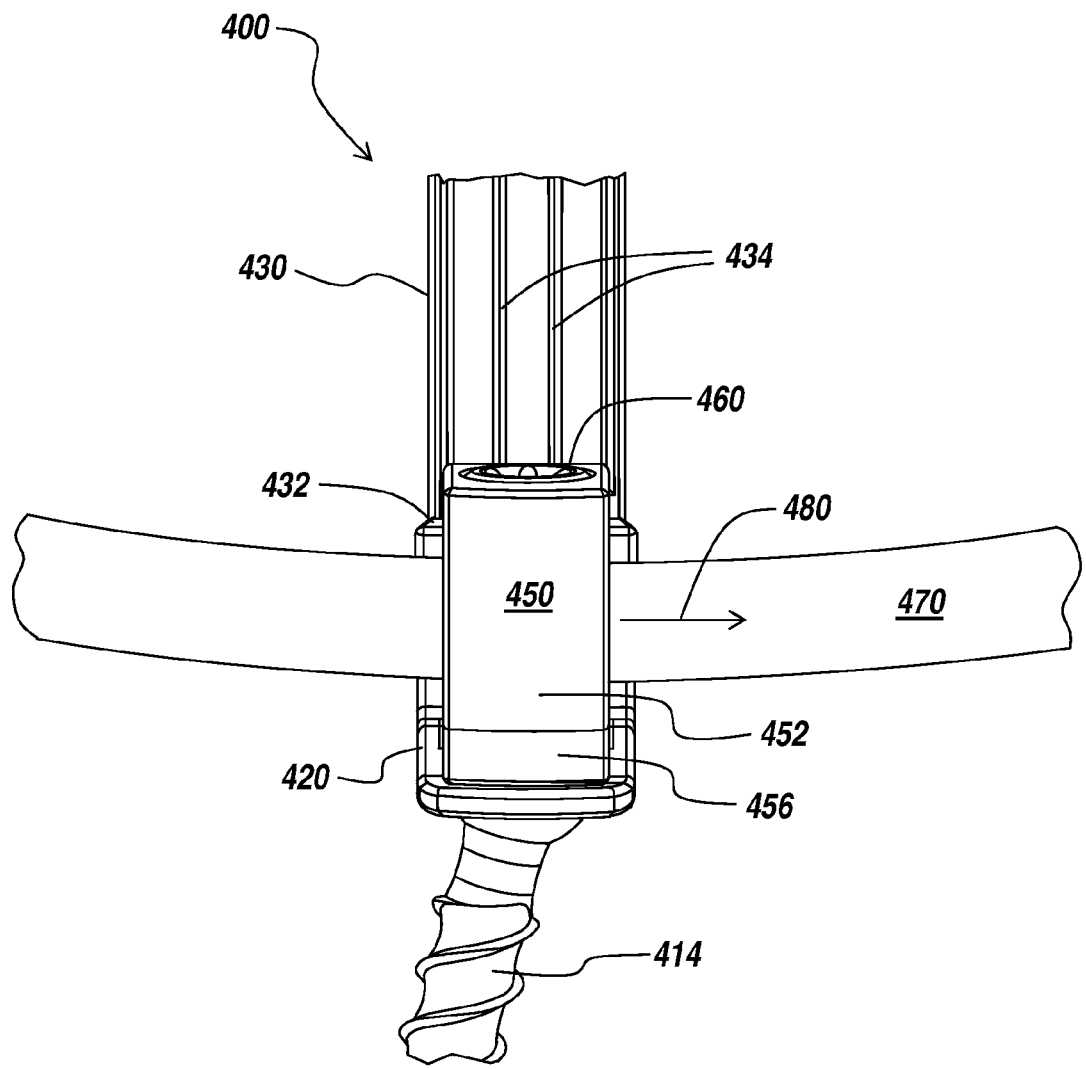
Figure 4F:
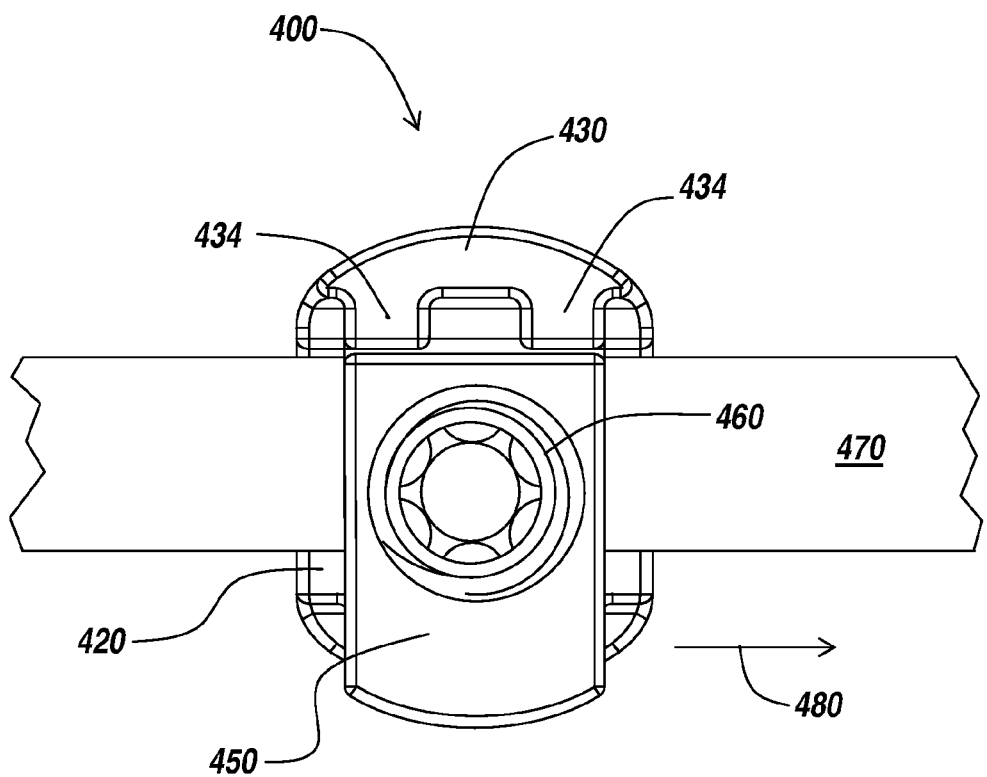

In FIGS. 4E and 4F, the cap 450 has been moved laterally in the direction indicated by arrow 480. When the cap 450 is moved laterally in such a fashion, the sliding lock features 456 engage the matching the matching features 426 on the connector body 420. Furthermore, the surface configuration 458 that allow the cap 450 to slide along the tracks 434 of the guide tab 430 are engaged by the ends of the tracks 434 in the relief section 432. Thus, by sliding the cap laterally in the direction indicated by arrow 480 the cap 450 is slidably mated with the connector body 420 thereby locking the cap 450 in place and capturing the spinal fixation element 470. In other embodiments, manipulation of the spinal fixation element 470 may cause the engagement of the matching locking features 426 and 456).

In the example of FIGS. 4A-4F, the implant 400 is further provided with a locking mechanism 460 in the form of a set screw. The set screw 460 may be used to secure the position of the spinal fixation element 470 and the connector body 420. The set screw 460 is configured to be inserted through the threaded passage 454 of the cap 450 to engage the spinal fixation element 470. In certain embodiments, the set screw 460 may be pre-loaded in the cap 450 when the cap 450 is inserted. When the set screw 460 is tightened, the set screw 460 pushes against and engages the spinal fixation element 470. The spinal fixation element 470 pushes against the saddle 440 sitting in the cavity 422 of the connector body 420 which in turn pushes against and engages the proximal head 412 of the bone anchor 410 passing through the cavity 422 of the connector body 420. Thus, by tightening the set screw 466, the positions of the spinal fixation element 470 and the connector body 420 are secured.

Once the positions of spinal fixation element 470 and connector body 420 have been secured using the set screw 460, the guide tab 430 may then be removed. As discussed previously, the guide tab 430 may have a break-away feature allowing the guide tab 430 to be detached and removed. Alternatively, the guide tab 430 can be detached by cutting the guide tab 430 away from the implant 400. In still other embodiments, the protrusion 430 may be mechanically attached such as through, a clamp, latch, dovetail, or the like, wherein the protrusion can be detached by disengaging the mechanical attachment. Other possible implementations and embodiments will be apparent to one skilled in the art given the benefit of this disclosure.

Figure 5A:
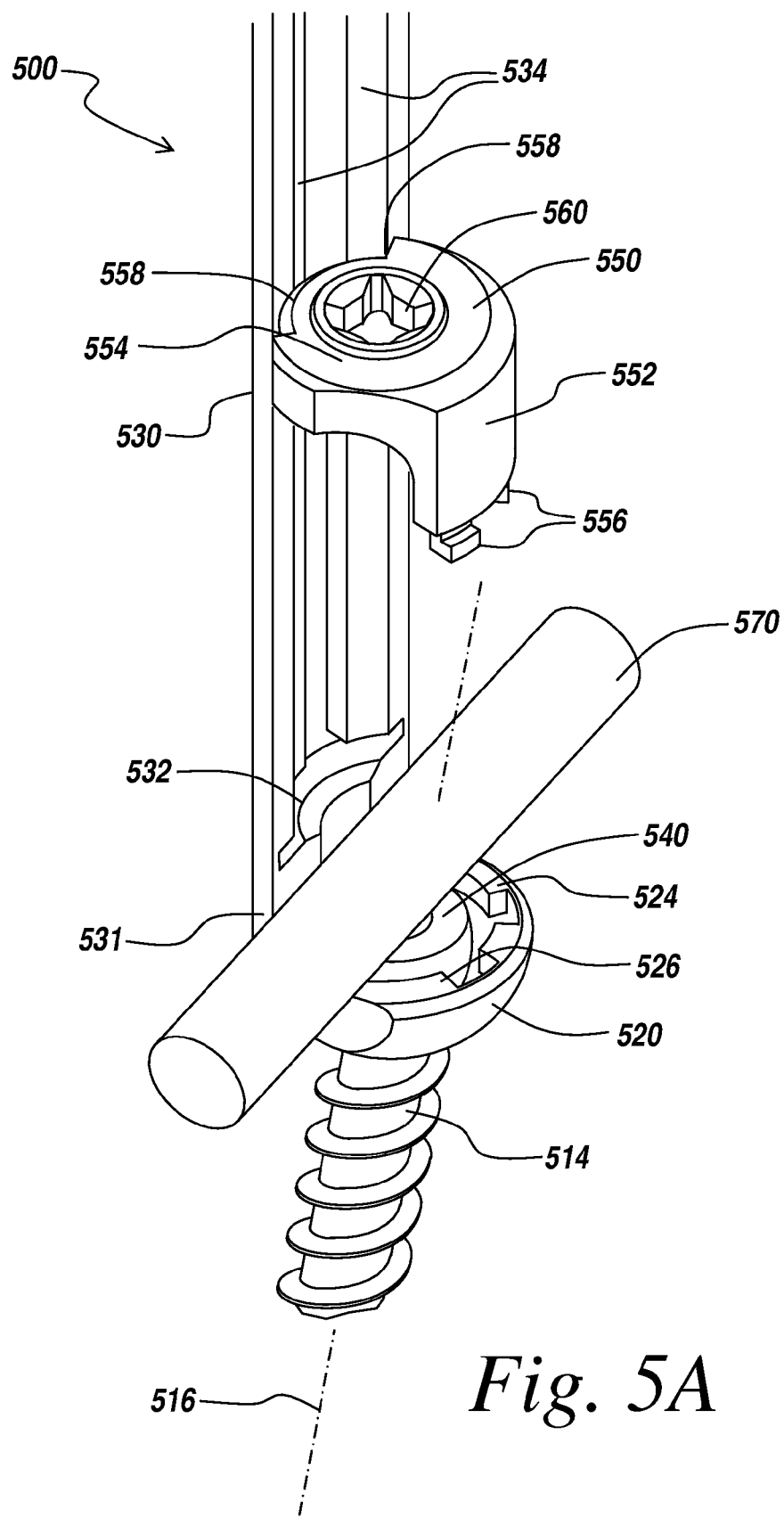
FIGS. 5A-5C illustrate another exemplary embodiment of an implant.
Figure 5B:
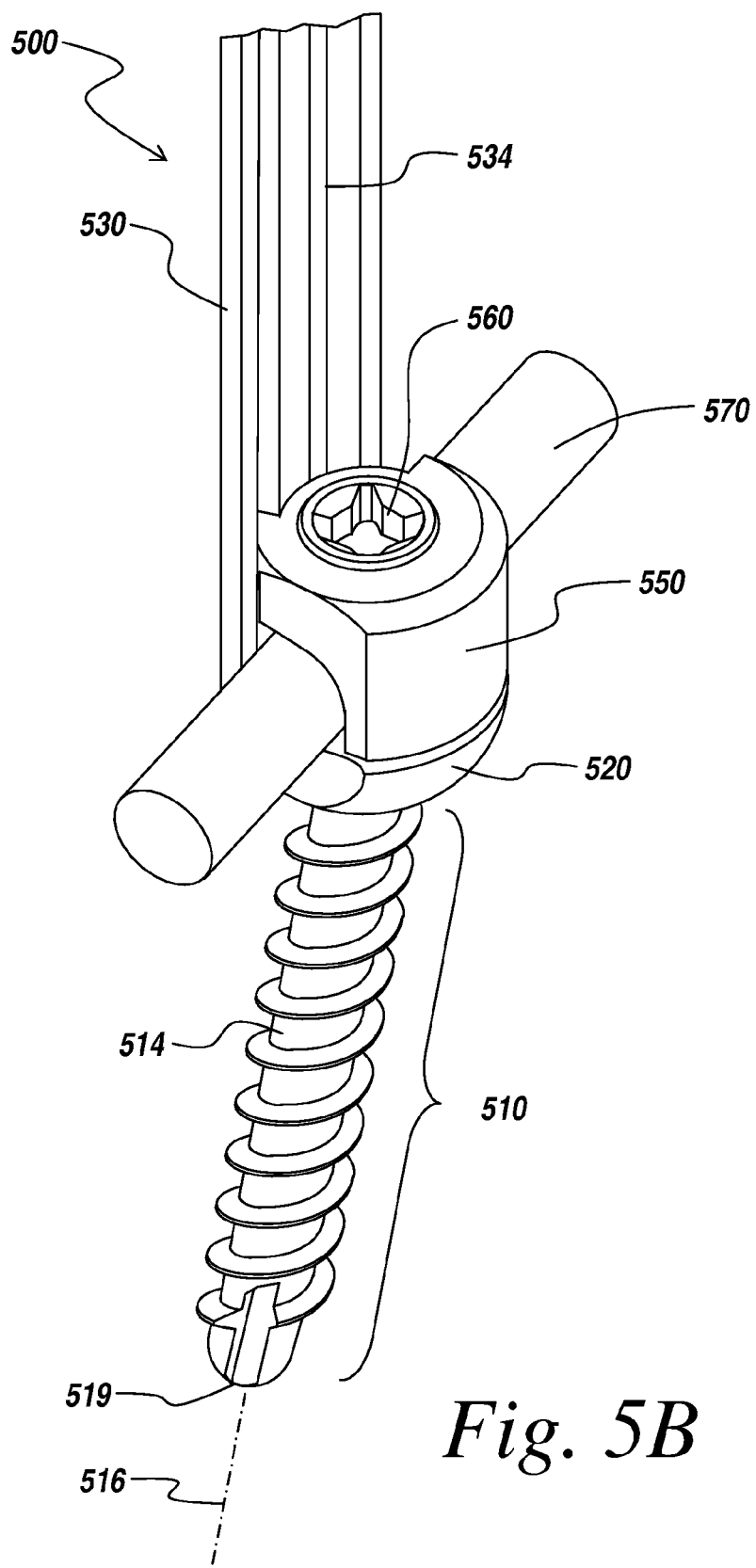
Figures 5C, 6:
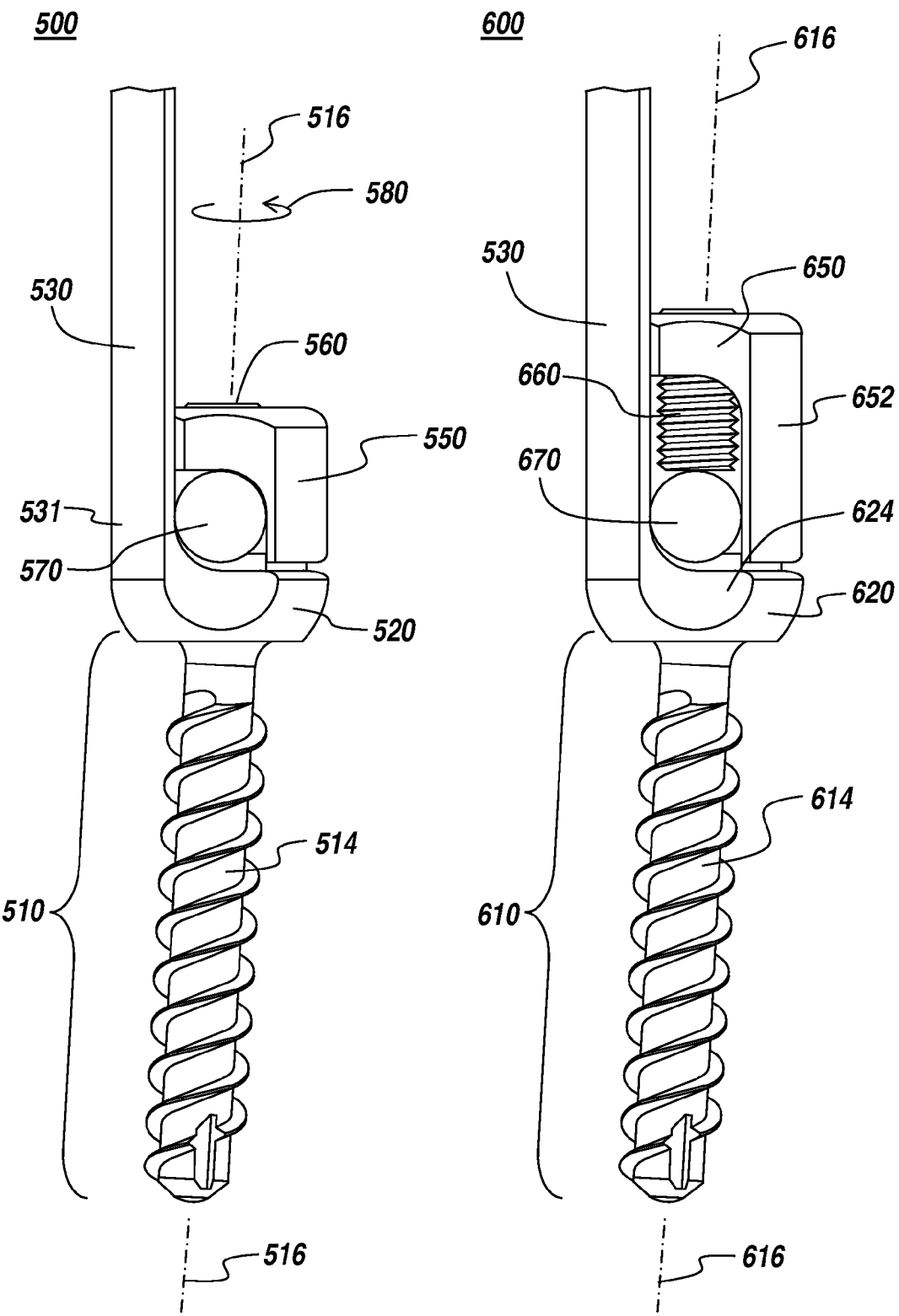
FIG. 6 illustrates another exemplary embodiment of an implant.

Another embodiment of an implant 500 can be seen in FIGS. 5A-5C. As with the previous embodiments, in this embodiment the implant 500 has a bone anchor 510, a connector body 520, and protrusion 530. As with FIGS. 3A and 3B, the bone anchor 510 and connector body 520 are already assembled. In this embodiment, the implant 500 further includes a saddle 540, a cap 550, and a locking mechanism 560.

In this example, the protrusion 530 is a guide tab that extends from the connector body 520 in the longitudinal axis 516 opposite and offset of the distal shaft 514 of the bone anchor 510. The guide tab 530 further defines a stop 531 at one end of the seat 524. The guide tab 530 is configured to extend outside the patient through the patient's skin while providing clear access to the connector body 520 and the proximal head of the bone anchor 510. Accordingly, the guide tab 530 may form a partial cannula extending through the skin wherein the guide tab has a crescent shaped cross section.

The guide tab 530 may have one or surface configurations 534 for engaging tools, spinal fixation elements, and/or closure mechanisms to further assist in the insertion and guidance of the tools, spinal fixation elements, and/or closure mechanisms. In the example of FIG. 5A-5C, the surface configurations 534 include tracks that mate with the cap 550 and guide the insertion of the cap 550.

The saddle 540 is provided as part of the implant 500. The saddle 540 is sized and configured to fit inside the cavity 522 in the connector body 520 and define the seat 524. In the examples of FIGS. 5A-C, the saddle 540 has already been inserted in the connector body 520 to define the seat 524.

In the examples of FIGS. 5A-5C, a closure mechanism 550 in the form of a cap is also provided. The cap 550 is configured to capture a spinal fixation element 570 on the saddle 540 defining the seat 524 of the connector body 520. The cap 550 includes a hook 552, a threaded passage 554, a twist lock feature 556, and surface configuration 558 for engaging the tracks 534 of the guide tab 530.

The hook 552 is configured to capture and hold the spinal fixation element 570 on the seat 524 of the connector body 520 thereby connecting the spinal fixation element 570 to the implant 500. The threaded passage 554 is configured to receive the locking mechanism 560. The twist lock feature 556 is configured to engage matching features 526 on the connector body 520. The surface configurations 558 are for mating with the tracks 534 of the guide tab 530.

The locking mechanism 560 is a set screw. The set screw 560 is configured to be inserted into the threaded passage 554 of the cap 550 engaging the threads of the threaded passage 554 of the cap 550 to secure the spinal fixation element 570.

In use, the implant 500 may be placed at a surgical site with the protrusion extending outside of the patient. In certain embodiments, the guide tab 530 may be used in the placement of the implant at the surgical site. In this example, the implant 500 including the bone anchor 510, connector body 520, and saddle 540 are pre-assembled before insertion and placement at a surgical side. As such, the saddle 540 is configured to allow access to the proximal head 514 of the bone anchor 510 after the saddle 540 has been inserted to allow for adjustment to the bone anchor 510.

Once the implant 500, including the bone anchor 510, connector body 520, and guide tab 530 are in place, a spinal fixation element 570 may be placed on the seat 524. The spinal fixation element 570 may be inserted before or after the implant 500 and then placed on the seat 524. In certain embodiments, the spinal fixation element may be inserted through the same incision used to insert the implant 500. In many instances, the implant, as well as the spinal fixation element 570, is inserted using minimally invasive surgical techniques. When using minimally invasive surgical techniques, visibility of the surgical site maybe limited. Thus the guide tab 530 extending out of the patient may provide a useful visual indicator for the position of the implant 500. The guide tab 530 may also serve as a physical guide for the placement of the spinal fixation element 570 on the seat 524 of the implant 500. As previously discussed, the guide tab 530 also defines a stop 531 at one end of the seat 524. Thus, when the spinal fixation device 570 hits the stop 531 defined by the guide tab 530, the user knows the spinal fixation device 570 is properly positioned on the seat 524. An example of this can be seen in FIG. 5A.

Once the spinal fixation element 570 has been seated on the implant 500, the cap 550 may be inserted to capture and retain the spinal fixation element 570 on the implant 500. The guide tab 530 extending outside the patient may serve as a guide for the insertion of the cap 550. The cap 550 has surface configurations 558 that mate with the tracks 534 of the guide tab 530 which hold the cap 550 in the correct orientation while the cap 550 is slid along the length of the guide tab 530 for insertion. Once at the surgical site, the hook 552 of the cap 550 captures and retains the spinal fixation element 570 on the seat 524 of the connector body 520. An example of this can be seen in FIG. 5B.

As previously mentioned, the cap 550 is provided with a twist lock feature 556. Once the cap 550 has captured the spinal fixation element 570 and mated with the connector body 520, the cap 550 may be further locked in position by rotating the cap 550 around a longitudinal axis 516 as shown in FIG. 5C. When the cap 550 is rotated, as indicated by arrow 580, the twist lock feature 556 on the cap 550 engage the matching features 526 on the connector body 520 to interconnect the cap 550 and connector body 520. Relief 532 allows mating feature 558 to rotate out of alignment features 534.

In the example of FIGS. 5A-5C, the implant 500 is further provided with a locking mechanism 560 in the form of a set screw. The set screw 560 may be used to secure the position of the spinal fixation element 570 and the connector body 520. The set screw 560 is configured to be inserted through the threaded passage 554 of the cap 550 to engage the spinal fixation element 570. In certain embodiments, the set screw 560 may be pre-loaded in the cap 550 when the cap 550 is inserted. When the set screw 560 is tightened, the set screw 560 pushes against and engages the spinal fixation element 570. The spinal fixation element 570 pushes against the saddle 540 sitting in the connector body 520 which in turn pushes against and engages the proximal head (not shown) of the bone anchor 510 passing through the connector body 520. Thus, by tightening the set screw 566, the positions of the spinal fixation element 570 and the connector body 520 are secured.

In certain other embodiment, the locking mechanism may also be used as part of a reduction technique. An example of this can be seen in FIG. 6.

In FIG. 6, a cap 650 with an elongated hook 652 is provided in conjunction with an elongated set screw 660. The rest of the implant 600 including the bone anchor 610, connector body 620, and protrusion 630 may be of the types described in the previous embodiments such as described in regard to FIGS. 4A-4F and 5A-5C. In this example, the spinal fixation element 670 will not properly sit on the seat 624 of the connector body 620. Hence, the cap 650 with the elongated hook 652 is used to capture the spinal fixation element 670. The cap 650 may engage and lock with the connector body 620 using any of the above techniques including the sliding lock feature 456 of FIGS. 4A-4F or the twist lock feature 556 of FIG. 5A-5C.

Once the spinal fixation element 670 has been captured, the elongated set screw 660 may be used to push the spinal fixation element 670 onto the seat 624 of the connector body 620 as seen in FIG. 6.

Once the positions of spinal fixation element (570 or 670) and connector body (520 or 620) have been secured using the set screw (560 or 660), the guide tab (530 or 630) may then be removed. The guide tab (530 or 630) may have a break-away feature allowing the guide tab (530 or 630) to be detached and removed. Alternatively, the guide tab (530 or 630) can be detached by cutting the guide tab (530 or 630) away from the implant (500 or 600). In still other embodiments, the protrusion (530 or 630) may be mechanically attached such as through, a clamp, latch, dovetail, or the like, wherein the protrusion can be detached by disengaging the mechanical attachment. Other possible implementations and embodiments will be apparent to one skilled in the art given the benefit of this disclosure.

Figure 7:
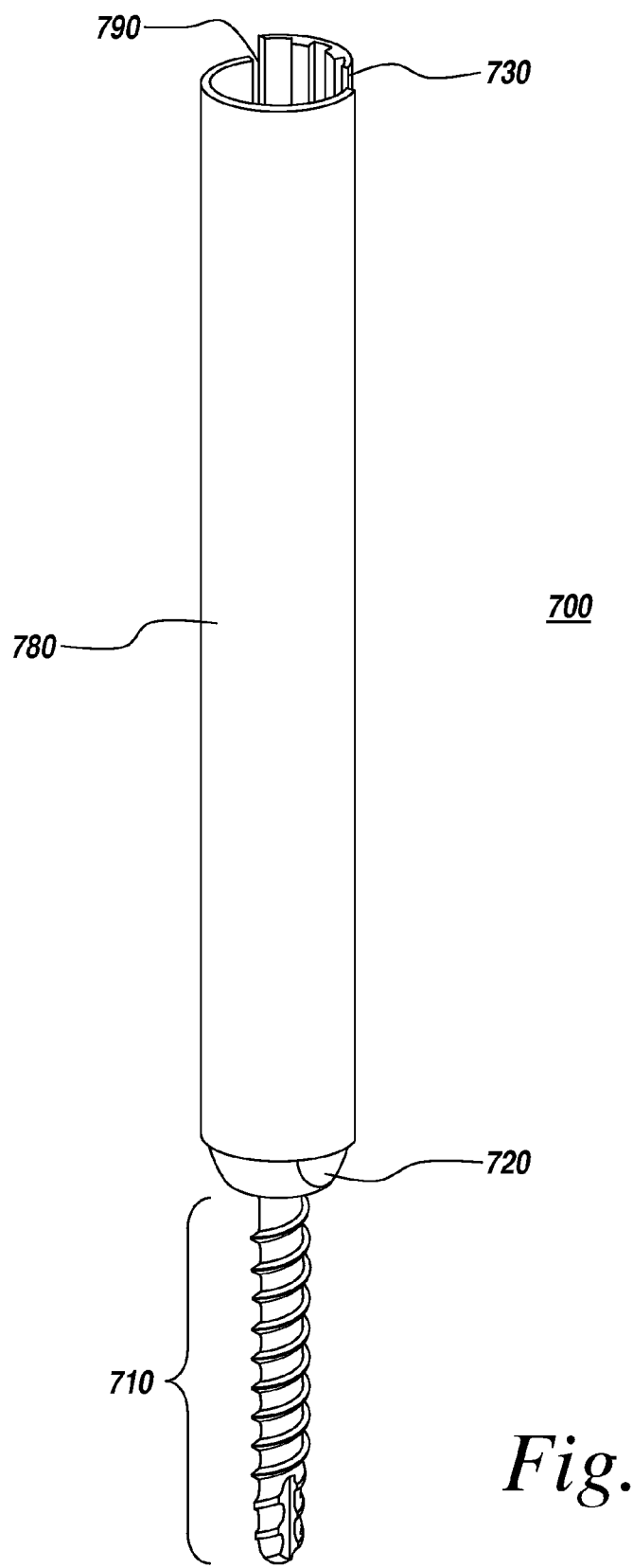
FIG. 7 illustrates an exemplary instrument for use with an embodiment of an implant.

FIG. 7 depicts and instrument 780 that may be used in conjunction with an implant 700 to form a cannula 790 to the surgical site. The instrument 780 may be any of the implants discussed previously having a bone anchor 710, connector body 720, and protrusion 730. Embodiments wherein the protrusion 730 is a guide tab having defining a partial cannula may particularly suitable for use with the instrument 780. The instrument 780 is shaped and configured to mate with the connector body 720 and protrusion 730 to define a cannula. In certain embodiments, the instrument may be able to interconnect or mate with the connector body 720 and/or protrusion 730 using the existing surface configurations on the connector body 720 and protrusion 730 such as, but not limited to, snap fit features, sliding lock features, twist lock features, dovetail features, and tracks. In other embodiments, interlocking features may be provided specifically to connect the instrument 780. When the instrument 780 is mated with the implant 700, the cannula 790 defined by the combination of the instrument 780 and implant 700 may be used for the insertion of other parts of the implant 700 such as, but not limited to, a bone anchor 710, a saddle (not shown), a cap (not shown), and a one or more locking members (not shown). In other embodiments, the instrument 780 may include pivotably connected to the implant, wherein the instrument may pivot out to capture a spinal fixation element (not shown) and then pivot back into position to secure the spinal fixation element. Other possible implementations and embodiments will be apparent to one skilled in the art given the benefit of this disclosure.

A person having ordinary skill in the art will appreciate that the aforementioned devices for securing a spinal fixation element can be modified depending on the type of spinal fixation element or implant being used, as well as the specific procedure being employed. Moreover, other methods and devices known in the art can be used in accordance with the present invention.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

While the instruments and methods of the present invention have been particularly shown and described with reference to the exemplary embodiments thereof, those of ordinary skill in the art will understand that various changes may be made in the form and details herein without departing from the spirit and scope of the present invention. Those of ordinary skill in the art will recognize or be able to ascertain many equivalents to the exemplary embodiments described specifically herein by using no more than routine experimentation. Such equivalents are intended to be encompassed by the scope of the present invention and the appended claims.

The invention claimed is:

1. An implant for use in a minimally invasive spinal fixation, the implant comprising:
   a bone anchor having a proximal head and a distal shaft extending along a longitudinal axis configured to engage bone;
   a connector body configured to engage the proximal head of bone anchor and engage a spinal fixation element; the connector body comprising:
      a cavity enclosed within the connector body for receiving the proximal head of the bone anchor;
      a seat formed on a top surface of the connector body for receiving the spinal fixation element, the seat being a substantially planar structure formed around a periphery of the enclosed cavity and constituting over half of the top surface of the connector body wherein the seat forms an outer periphery of the top surface of the connector body; and
      wherein the connector body slopes longitudinally upward from the seat to form a stop for the spinal fixation element at one end of the connector body;
   a protrusion for aiding in insertion and placement of the implant and the spinal fixation element extending from the connector body along a longitudinal axis opposite and offset of the distal shaft of the bone anchor, wherein the protrusion forms a partial cannula and has a crescent shaped cross-section.

2. The implant of claim 1, wherein the connector body further comprises a saddle defining the seat for receiving the spinal fixation element.

3. The implant of claim 1, wherein the protrusion is detachable from the connector body.

4. The implant of claim 1, wherein the protrusion comprises a guide tab.

5. The implant of claim 4, wherein the guide tab further comprises surface configurations for engaging at least one of, a saddle, a cap, a locking mechanism, and an instrument.

6. The implant of claim 1, further comprising a cap configured to be inserted along the protrusion for capturing the spinal fixation element on the connector body.

7. The implant of claim 6, further including a locking mechanism for securing the cap on the connector body.

8. The implant of claim 6, wherein the cap is configured to mate with the connector body with a snap fit.

9. The implant of claim 6, wherein the cap is configured to slideably mate with the connector body.

10. The implant of claim 6, wherein the cap is configured to mate with the connector body with a twist-lock.

11. An implant for use in a minimally invasive spinal fixation, the implant comprising:
 a bone anchor having a proximal head that is spherically shaped and a distal shaft extending along a longitudinal axis configured to engage bone;
 a connector body configured to engage the proximal head of bone anchor and engage a spinal fixation element, the connector body comprising:
  a cavity enclosed within the connector body for receiving the proximal head of the bone anchor;
  a saddle defining a seat formed on a top surface of the connector body for receiving the spinal fixation element, wherein the saddle is shaped to mate with the spherically shaped proximal head of the bone anchor, the seat being a substantially planar structure formed around a periphery of the enclosed cavity and constituting over half of the top surface of the connector body wherein the seat forms an outer periphery of the top surface of the connector body; and
  wherein the connector body slopes longitudinally upward from the seat to form a stop for the spinal fixation element at one end of the connector body;
 wherein the bone anchor is configured to pivot in multiple directions relative to the connector body,
 a detachable tab for aiding in insertion and placement of the implant and the spinal fixation element extending from the connector body along a longitudinal axis opposite and offset of the distal shaft of the bone anchor,
 a cap for capturing the spinal fixation element on the connector body, wherein the cap includes configurations that mate with surface configurations of the tab to hold the cap in a correct orientation while slid along the tab for insertion.

12. The implant of claim 11, further including a locking mechanism for securing the cap and spinal fixation element on the connector body.

13. The implant of claim 11, wherein the cap is configured to mate with the connector body with a snap fit.

14. An implant for use in a minimally invasive spinal fixation, the implant comprising:
 a bone anchor having a proximal head that is spherically shaped and a distal shaft extending along a longitudinal axis configured to engage bone;
 a connector body configured to engage the proximal head of bone anchor and engage a spinal fixation element; the connector body comprising:
  surface configurations;
  a cavity enclosed within the connector body for receiving the proximal head of the bone anchor;
  a saddle defining a seat formed on a top surface of the connector body for receiving the spinal fixation element wherein the saddle is shaped to mate with the spherically shaped proximal head of the bone anchor, the seat being a substantially planar structure formed around a periphery of the enclosed cavity and constituting over half of the top surface of the connector body wherein the seat forms an outer periphery of the top surface of the connector body; and
  wherein the connector body slopes longitudinally upward from the seat to form a stop for the spinal fixation element at one end of the connector body;
 wherein the bone anchor is configured to pivot in multiple directions relative to the connector body;
 a detachable guide tab for aiding in insertion and placement of the implant and the spinal fixation element extending from the connector body along a longitudinal axis opposite and offset of the distal shaft of the bone anchor and having surface configuration for engaging at least one of, a saddle, a cap, a locking mechanism, and an instrument,
 a cap configured to be inserted along the guide tab for capturing the spinal fixation element on the connector body, wherein the cap includes a snap-fit feature to provide a snap-fit connection and to provide audible and tactile feedback that the spinal fixation element has been captured during implantation; and wherein the snap-fit feature comprises a deformable finger with surface configurations that engage the surface configurations of the connector body to provide the audible and tactile feedback.

15. The implant of claim 14, further including a locking mechanism for securing the cap and spinal fixation element on the connector body.

16. The implant of claim 14, further including a second locking mechanism for securing the cap and spinal fixation element on the connector body.

* * * * *